(12) United States Patent
Labit

(10) Patent No.: US 8,409,163 B2
(45) Date of Patent: Apr. 2, 2013

(54) REUSABLE DIAPERS HAVING FIRST AND SECOND LIQUID-ABSORBENT FLAPS

(76) Inventor: Jennifer Lynn Labit, Arnold, MO (US)

( * ) Notice: Subject to any disclaimer, the term of this patent is extended or adjusted under 35 U.S.C. 154(b) by 0 days.

(21) Appl. No.: 13/344,785

(22) Filed: Jan. 6, 2012

(65) Prior Publication Data

US 2012/0116340 A1    May 10, 2012

Related U.S. Application Data

(63) Continuation of application No. 13/229,104, filed on Sep. 9, 2011, which is a continuation-in-part of application No. 12/059,856, filed on Mar. 31, 2008, which is a continuation-in-part of application No. 11/518,587, filed on Sep. 8, 2006, now Pat. No. 7,629,501.

(51) Int. Cl.
*A61F 13/539* (2006.01)

(52) U.S. Cl. .......................... 604/400; 604/377; 604/397

(58) Field of Classification Search .................. 604/377, 604/397–398, 400
See application file for complete search history.

(56) References Cited

U.S. PATENT DOCUMENTS

| | | |
|---|---|---|
| 1,003,399 A | 9/1911 | Burns |
| 1,961,515 A | 6/1934 | Friedman |
| 2,016,355 A | 10/1935 | Alsop |
| 2,049,913 A | 8/1936 | Lesueur |
| RE20,315 E | 3/1937 | Lesueur |
| 2,292,030 A | 8/1942 | Kraft |
| 2,450,059 A | 9/1948 | Rickerson |
| 2,468,445 A | 4/1949 | Hurst |
| 2,493,492 A | 1/1950 | Malamut |
| 2,523,079 A | 9/1950 | Walter et al. |
| 2,532,029 A | 11/1950 | Medoff |
| 2,545,216 A | 3/1951 | Toussie |
| 2,568,590 A | 9/1951 | Laser |
| 2,575,164 A | 11/1951 | Donovan |
| 2,577,398 A | 12/1951 | Blake |
| 2,581,904 A | 1/1952 | Burns |
| 2,591,079 A | 4/1952 | Leaton |
| 2,605,558 A | 8/1952 | Kennette |

(Continued)

FOREIGN PATENT DOCUMENTS

| | | |
|---|---|---|
| AU | 5039493 | 1/1994 |
| AU | 9539089 | 6/1996 |

(Continued)

OTHER PUBLICATIONS

Biodegradable Diapers, Real user reviews of Biodegradable Diapers, diapers that are good for babies, parents and the planet, CuteyBaby "One and Done!" Modern Cloth Diaper Starter Kit—GIRL, 5 pages, (Customer Review, Mar. 22, 2011) biodegradablediapers.info.

(Continued)

*Primary Examiner* — Susan Su
(74) *Attorney, Agent, or Firm* — Harness, Dickey & Pierce, P.L.C.

(57) ABSTRACT

A reusable diaper includes a forward waist portion, a rearward waist portion, and a crotch portion between the forward waist portion and the rearward waist portion. The diaper also includes first and second liquid-absorbent flaps. Each flap may have a fixed end portion coupled to the diaper and a free end portion opposite the fixed end portion, which is not coupled to the reusable diaper. The first and second liquid-absorbent flaps may be positionable in an overlapping manner along the crotch portion with one of the first and second liquid-absorbent flaps overlapped by the other one of said first and second liquid-absorbent flaps and slidable relative to each other when overlapped. In some embodiments, the first and second liquid-absorbent flaps may each include an at least partially hollow interior and an opening for allowing airflow into the hollow interior to facilitate drying.

19 Claims, 13 Drawing Sheets

U.S. PATENT DOCUMENTS

| | | | |
|---|---|---|---|
| 2,607,348 A | 8/1952 | Rosenblatt | |
| 2,627,859 A | 2/1953 | Hargrave | |
| 2,664,895 A | 1/1954 | Shulman | |
| 2,688,328 A | 9/1954 | Marcus | |
| 2,703,577 A | 3/1955 | May | |
| 2,733,715 A | 2/1956 | Folk | |
| 2,788,786 A | 4/1957 | Dexter | |
| 2,826,199 A | 3/1958 | Brandon | |
| 2,853,073 A | 9/1958 | Brafman | |
| 2,866,459 A | 12/1958 | Sobelson | |
| 2,868,205 A | 1/1959 | Epstein | |
| 2,893,393 A | 7/1959 | Pressley | |
| 2,910,982 A | 11/1959 | Woodward | |
| 2,985,170 A | 5/1961 | Title | |
| 3,049,124 A | 8/1962 | Thompson | |
| 3,141,461 A | 7/1964 | Farris | |
| 3,162,196 A | 12/1964 | Salk | |
| 3,341,394 A | 9/1967 | Kinney | |
| 3,485,706 A | 12/1969 | Evans | |
| 3,530,859 A | 9/1970 | Helmowitz | |
| 3,559,648 A | 2/1971 | Mason, Jr. | |
| 3,658,064 A | 4/1972 | Pociluyko | |
| 3,667,466 A | 6/1972 | Ralph | |
| 3,741,212 A | 6/1973 | Schutte | |
| 3,769,978 A | 11/1973 | DeNight et al. | |
| 3,882,871 A | 5/1975 | Taniguchi | |
| RE28,483 E | 7/1975 | Ralph | |
| 3,926,189 A | 12/1975 | Taylor | |
| 4,037,602 A | 7/1977 | Hawthorne | |
| 4,338,939 A | 7/1982 | Daville | |
| D269,907 S | 7/1983 | Tong | |
| 4,414,971 A | 11/1983 | Chung et al. | |
| 4,548,604 A | 10/1985 | Ellsworth | |
| 4,568,342 A | 2/1986 | Davis | |
| 4,573,987 A | 3/1986 | Lamb, Jr. | |
| 4,643,726 A | 2/1987 | Gegelys | |
| 4,671,793 A | 6/1987 | Hults et al. | |
| 4,681,581 A | 7/1987 | Coates | |
| 4,695,279 A | 9/1987 | Steer | |
| 4,704,117 A | 11/1987 | Mitchell | |
| 4,773,906 A * | 9/1988 | Krushel | 604/391 |
| 4,834,737 A | 5/1989 | Khan | |
| 4,850,987 A * | 7/1989 | Gilomen | 604/385.15 |
| 4,892,598 A | 1/1990 | Stevens et al. | |
| 4,904,251 A | 2/1990 | Igaue et al. | |
| 4,906,243 A | 3/1990 | Dravland | |
| 4,928,323 A | 5/1990 | Nathan | |
| 4,950,263 A | 8/1990 | Lewis | |
| 4,961,736 A | 10/1990 | McCloud | |
| 4,978,345 A | 12/1990 | Holiday et al. | |
| 4,981,480 A * | 1/1991 | Gaudet et al. | 604/386 |
| 5,019,068 A * | 5/1991 | Perez et al. | 604/386 |
| 5,069,672 A * | 12/1991 | Wippler et al. | 604/385.14 |
| 5,100,399 A * | 3/1992 | Janson et al. | 604/386 |
| 5,106,382 A | 4/1992 | Henry | |
| 5,108,385 A | 4/1992 | Snyder | |
| 5,135,522 A | 8/1992 | Fahrenkrug et al. | |
| 5,137,526 A | 8/1992 | Coates | |
| 5,185,011 A | 2/1993 | Strasser | |
| 5,188,626 A | 2/1993 | Toyoda et al. | |
| 5,207,662 A | 5/1993 | James | |
| 5,217,447 A | 6/1993 | Gagnon | |
| D339,633 S | 9/1993 | Porter | |
| 5,306,267 A | 4/1994 | Hahn et al. | |
| 5,325,543 A | 7/1994 | Allen | |
| 5,342,340 A | 8/1994 | Kichefski et al. | |
| 5,360,422 A | 11/1994 | Brownlee et al. | |
| 5,368,585 A * | 11/1994 | Dokken | 604/393 |
| D354,809 S | 1/1995 | Eskey | |
| 5,399,177 A | 3/1995 | Blaney et al. | |
| 5,405,342 A | 4/1995 | Roessler et al. | |
| 5,409,476 A | 4/1995 | Coates | |
| D362,717 S | 9/1995 | Caschette et al. | |
| 5,454,799 A | 10/1995 | Lakiss-Smith et al. | |
| 5,458,591 A | 10/1995 | Roessler et al. | |
| 5,476,457 A | 12/1995 | Roessler et al. | |
| D366,112 S | 1/1996 | Tollin et al. | |
| 5,514,121 A | 5/1996 | Roe et al. | |
| 5,527,300 A | 6/1996 | Sauer | |
| 5,611,789 A | 3/1997 | Seth | |
| 5,613,959 A | 3/1997 | Roessler et al. | |
| D386,582 S | 11/1997 | Levine | |
| 5,695,488 A | 12/1997 | Sosalla | |
| 5,706,524 A | 1/1998 | Herrin et al. | |
| 5,722,127 A | 3/1998 | Coates | |
| 5,725,518 A | 3/1998 | Coates | |
| 5,814,037 A | 9/1998 | Coates | |
| 5,853,403 A | 12/1998 | Tanzer et al. | |
| 5,891,122 A | 4/1999 | Coates | |
| D436,400 S | 1/2001 | Kiecker | |
| 6,168,583 B1 | 1/2001 | Tanji et al. | |
| 6,193,702 B1 | 2/2001 | Spencer | |
| 6,254,583 B1 | 7/2001 | Coates | |
| 6,315,764 B1 | 11/2001 | Faulks et al. | |
| 6,322,552 B1 | 11/2001 | Blenke et al. | |
| 6,379,343 B2 | 4/2002 | Stephenson et al. | |
| 6,383,170 B1 | 5/2002 | Mishima et al. | |
| 6,402,731 B1 | 6/2002 | Surprise et al. | |
| 6,423,047 B1 | 7/2002 | Webster | |
| 6,471,681 B1 | 10/2002 | Ronnberg et al. | |
| 6,482,194 B1 | 11/2002 | Putzer | |
| 6,540,730 B1 | 4/2003 | Niedermeyer | |
| 6,562,016 B2 | 5/2003 | Shinkai | |
| 6,569,137 B2 | 5/2003 | Suzuki et al. | |
| 6,579,273 B2 | 6/2003 | Dupuy | |
| 6,616,645 B1 | 9/2003 | Moravek | |
| 6,623,466 B1 | 9/2003 | Richardson | |
| 6,641,569 B1 | 11/2003 | Coles et al. | |
| 6,766,817 B2 | 7/2004 | da Silva | |
| 6,767,498 B1 | 7/2004 | Talley et al. | |
| 6,918,404 B2 | 7/2005 | Dias da Silva et al. | |
| 6,932,800 B2 | 8/2005 | LaVon et al. | |
| 6,989,005 B1 | 1/2006 | LaVon et al. | |
| 7,066,586 B2 | 6/2006 | da Silva et al. | |
| 7,244,398 B2 | 7/2007 | Kotary et al. | |
| 7,264,615 B2 | 9/2007 | Sherrod et al. | |
| 7,285,255 B2 | 10/2007 | Kadlec et al. | |
| 7,361,803 B2 | 4/2008 | Miskie | |
| 7,591,811 B2 | 9/2009 | Crislip Wilkinson | |
| 7,629,501 B2 | 12/2009 | Labit et al. | |
| D610,255 S * | 2/2010 | Garner | D24/126 |
| D610,256 S * | 2/2010 | Garner | D24/126 |
| 2002/0010452 A1 | 1/2002 | Dupuy | |
| 2002/0094740 A1 | 7/2002 | Li et al. | |
| 2003/0014024 A1 | 1/2003 | Kiecker | |
| 2003/0083635 A1 | 5/2003 | Gibbs | |
| 2003/0109841 A1 | 6/2003 | Edwards | |
| 2004/0044323 A1 | 3/2004 | Roessler et al. | |
| 2004/0082933 A1 | 4/2004 | Karami | |
| 2004/0236298 A1 | 11/2004 | Coates | |
| 2004/0236300 A1 | 11/2004 | Gibbs et al. | |
| 2004/0267219 A1 | 12/2004 | Olmedo | |
| 2005/0085784 A1 | 4/2005 | LeMinh et al. | |
| 2005/0148258 A1 | 7/2005 | Chakravarty et al. | |
| 2005/0210560 A1 | 9/2005 | Coates | |
| 2005/0228356 A1 | 10/2005 | LaVon et al. | |
| 2006/0167432 A1 | 7/2006 | Sigari | |
| 2007/0066952 A1 | 3/2007 | LaVon et al. | |
| 2008/0015531 A1 | 1/2008 | Hird et al. | |
| 2008/0065039 A1 | 3/2008 | Labit et al. | |
| 2008/0183148 A1 | 7/2008 | Labit et al. | |
| 2010/0036340 A1 | 2/2010 | Allison-Rogers | |
| 2010/0087794 A1 | 4/2010 | Labit et al. | |
| 2010/0108554 A1 | 5/2010 | Melius et al. | |
| 2010/0130955 A1 | 5/2010 | Tice | |
| 2011/0137278 A1 | 6/2011 | Ormsby et al. | |
| 2011/0301561 A1* | 12/2011 | Tournier | 604/377 |
| 2011/0319852 A1 | 12/2011 | Labit | |
| 2012/0172827 A1 | 7/2012 | Dupuy | |

FOREIGN PATENT DOCUMENTS

| | | |
|---|---|---|
| BR | 03606/71 | 12/1971 |
| BR | 360571 | 12/1971 |
| CA | 2024375 | 3/1992 |
| CA | 2097437 | 12/1993 |
| CA | 2103537 A | 2/1995 |
| DE | 4326271 | 2/1995 |

| | | |
|---|---|---|
| EP | 0099846 | 2/1984 |
| EP | 0486006 | 11/1991 |
| EP | 0475702 | 3/1992 |
| EP | 2106775 | 10/2009 |
| ES | 2115559 | 6/1998 |
| GB | 493819 | 10/1938 |
| GB | 0849573 | 9/1960 |
| GB | 0803716.0 | 2/2008 |
| JP | 04150853 | 5/1992 |
| JP | 08000662 | 1/1996 |
| WO | WO-87/05471 | 9/1987 |
| WO | WO-90/07313 | 7/1990 |
| WO | WO-94/03137 | 2/1994 |
| WO | WO 94/15563 | 7/1994 |
| WO | WO-95/23569 | 9/1995 |
| WO | WO-98/24388 | 6/1998 |
| WO | WO-99/33421 | 7/1999 |
| WO | WO-2008/030984 | 3/2008 |
| WO | WO-2008/142634 | 11/2008 |
| WO | WO-2009/106899 | 9/2009 |
| WO | WO-2009/146021 | 12/2009 |
| ZA | 8701842 | 11/1988 |

OTHER PUBLICATIONS

Biodegradable Diapers, Real user reviews of Biodegradable Diapers, diapers that are good for babies, parents and the planet, CuteyBaby "One and Done!" Modern Cloth Diaper Starter Kit—GIRL, 5 pages, (Customer Review, Jun. 3, 2010) biodegradablediapers.info.
Biodegradable Diapers, Real user reviews of Biodegradable Diapers, diapers that are good for babies, parents and the planet, CuteyBaby "One and Done!" Modern Cloth Diaper Starter Kit—GIRL, 5 pages, (Customer Review, May 22, 2010) biodegradablediapers.info.
Derwent abstract and Figure of CA 2024375A, publication date Mar. 1, 1992.
FuzziBunz, A better diaper for a better planet, Newsletter, FuzziBunz Press Releases, 2 pages, (Jul. 10, 2007).
http://fuzzibunz.com/Fuzzi-Bunz-Colors.htm, 2 pages, accessed and printed Sep. 8, 2006.
http://getantsy.com/Antsy-Pants-Are.html, Antsy Pants™ Pull-Up Cloth Diapers, Optimized for Potty Training, 2009-2011, 6 pages, accessed and printed Sep. 21, 2011.
http://hydrology-tubarc.blogspot.com/32 pages, accessed Sep. 15, 2008.
http://ip-know-how-tubarc.blogspot.com/, 8 pages, accessed Sep. 15, 2008.
http://tubarc.blogspot.com/, 206 pages, accessed Sep. 15, 2008.
http://web.archive.org/web/20041010045134/www.changingbabies.com/anatomyofadiaper.html, accessed Apr. 27, 2007, 17 pages.
http://www.cottonbabies.com/index.php, 7 pages, accessed on Aug. 24, 2006.
http://www.diapersite.com/baby_diapers_specs.htrn, 4 pages, accessed Apr. 23, 2008.
http://www.diapersite.com/images/diaperspecs/velcro.htm, 1 page, accessed Apr. 23, 2008.
http://www.gro-via.com/aiotutorial.html, 2011 The Natural Baby Company, 4 pages, accessed and printed Sep. 21, 2011.
http://www.tinytush.com/, 6 pages, accessed and printed Sep. 8, 2006.
http://www.wonderworksbabyco.com/products.htm, 5 pages, accessed and printed Sep. 8, 2006.
http:www.aplix.com/en/layout/set/print/content/search, accessed Apr. 27, 2007, 3 pages.
https://www.gro-via.com/mychoice-trainer.html, 2011 The Natural Baby Company, 5 pages, accessed and printed Sep. 21, 2011.
Definition of "Waterproof", Webster's Third New International Dictionary, unabridged, 1993, 1 page.

* cited by examiner

REUSABLE DIAPERS HAVING FIRST AND SECOND LIQUID-ABSORBENT FLAPS

CROSS-REFERENCE TO RELATED APPLICATIONS

This application is a continuation of U.S. patent application Ser. No. 13/229,104 filed Sep. 9, 2011 (published Dec. 29, 2011 as US 2011/0319852) which, in turn, is a continuation-in-part of U.S. patent application Ser. No. 12/059,856 filed Mar. 31, 2008 (published Jul. 31, 2008 as US 2008/0183148), which, in turn, is a continuation-in-part of U.S. patent application Ser. No. 11/518,587 filed Sep. 8, 2006 (now U.S. Pat. No. 7,629,501 issued Dec. 8, 2009). The entire disclosures of each of the above applications are incorporated herein by reference.

FIELD

The present disclosure relates generally to reusable diapers.

BACKGROUND

This section provides background information related to the present disclosure which is not necessarily prior art.

Absorbent articles, such as disposable diapers, training pants, or incontinence pads, generally have an absorbent core intended for single use only. Once the absorbent core component is saturated with bodily discharges, such as urine, the entire absorbent article is usually discarded. Oftentimes, parts of a disposable diaper or training pants could be reused. But with the unitary construction, they are nevertheless discarded along with the saturated absorbent cores. In addition to the added cost and waste associated with discarding such products, it is often inconvenient to acquire and store quantities of such disposable absorbent articles.

SUMMARY

This section provides a general summary of the disclosure, and is not a comprehensive disclosure of its full scope or all of its features.

According to various aspects, exemplary embodiments of reusable diapers are disclosed herein. In an exemplary embodiment, a reusable diaper generally includes a forward waist portion, a rearward waist portion, and a crotch portion between the forward waist portion and the rearward waist portion. The diaper also includes first and second liquid-absorbent flaps each having a fixed end portion coupled to the diaper and a free end portion opposite the fixed end portion, which is not coupled to the reusable diaper. The first and second liquid-absorbent flaps are positionable in an overlapping manner along the crotch portion with one of the first and second liquid-absorbent flaps overlapped by the other one of said first and second liquid-absorbent flaps and slidable relative to each other when overlapped.

In another exemplary embodiment, a reusable diaper includes a forward waist portion, a rearward waist portion, and a crotch portion between the forward waist portion and the rearward waist portion. The diaper also includes first and second liquid-absorbent flaps for providing one or more liquid absorbing layers within the diaper. Each of the first and second liquid-absorbent flaps includes an at least partially hollow interior and an opening for allowing airflow into the hollow interior to facilitate drying.

In a further exemplary embodiment, a reusable diaper includes a forward waist portion, a rearward waist portion, and a crotch portion between the forward waist portion and the rearward waist portion. The diaper also includes at least one inner layer configured to be liquid-absorbent and at least one outer layer configured to be substantially liquid-impervious and coupled to the inner layer. A first liquid-absorbent flap has a fixed end portion coupled to the inner layer and a free end portion opposite the fixed end portion, which is not coupled to the reusable diaper. The first liquid-absorbent flap includes an at least partially hollow interior and an opening for allowing airflow into the hollow interior to facilitate drying of the first liquid-absorbent flap. A second liquid-absorbent flap has a fixed end portion coupled to the inner layer and a free end portion opposite the fixed end portion, which is not coupled to the reusable diaper. The second liquid-absorbent flap includes an at least partially hollow interior and an opening for allowing airflow into the hollow interior to facilitate drying of the second liquid-absorbent flap.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

Figure 1:
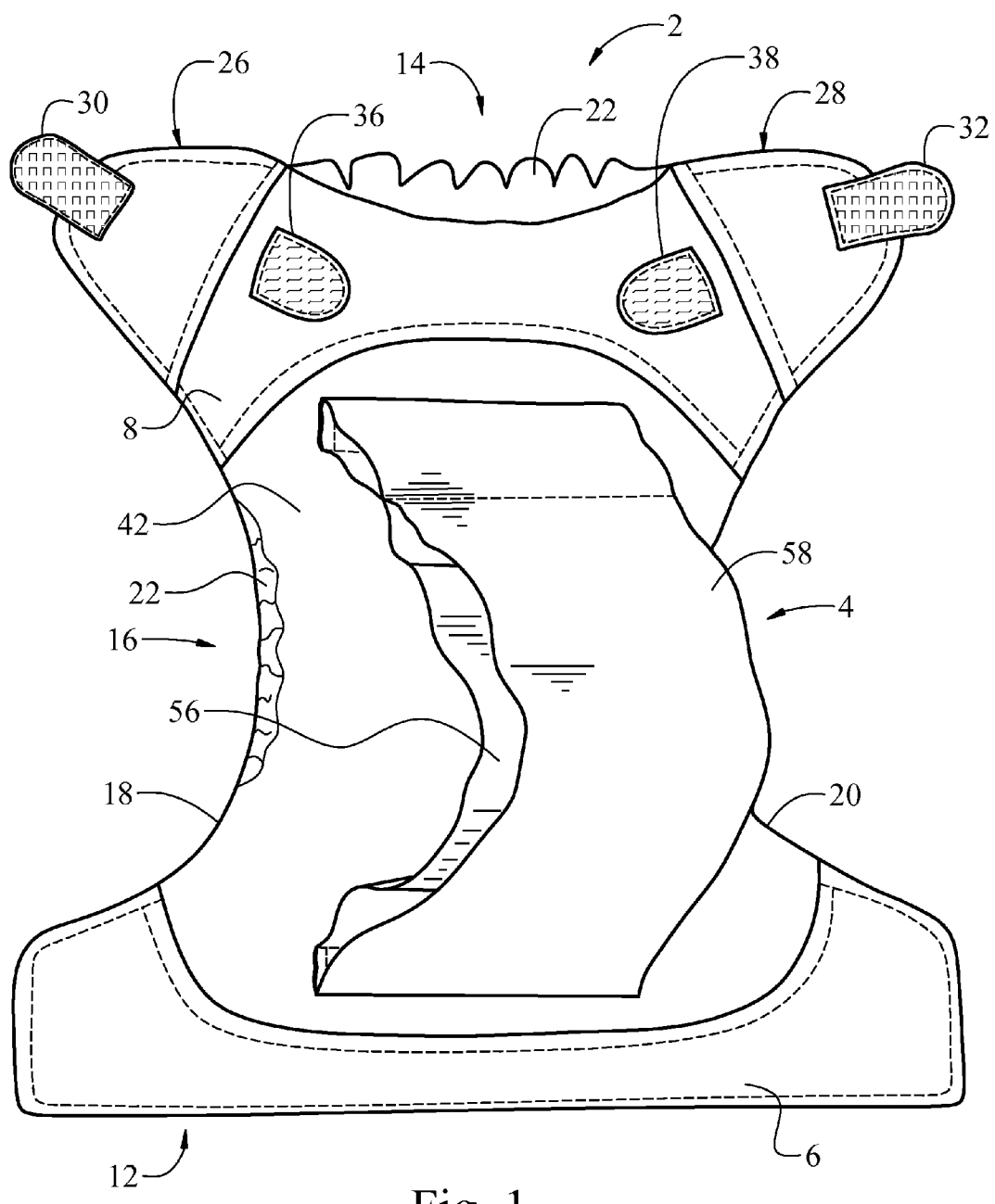
FIG. 1 is an inner perspective view of an exemplary embodiment of a gender neutral reusable diaper having an adjustable fluid-absorbing insert for use in absorbing fluids within the reusable diaper.

The following description is merely exemplary in nature and is not intended to limit the present disclosure, application, or uses. It should be understood that throughout the drawings, corresponding reference numerals indicate like or corresponding parts and features.

According to various aspects, exemplary embodiments of reusable diapers are disclosed herein. In an exemplary embodiment, a reusable diaper generally includes a forward waist portion, a rearward waist portion, and a crotch portion between the forward waist portion and the rearward waist portion. The diaper also includes first and second liquid-absorbent flaps each having a fixed end portion coupled to the diaper and a free end portion opposite the fixed end portion, which is not coupled to the reusable diaper. The first and second liquid-absorbent flaps are positionable in an overlapping manner along the crotch portion with one of the first and second liquid-absorbent flaps overlapped by the other one of said first and second liquid-absorbent flaps and slidable relative to each other when overlapped.

In another exemplary embodiment, a reusable diaper includes a forward waist portion, a rearward waist portion, and a crotch portion between the forward waist portion and the rearward waist portion. The diaper also includes first and second liquid-absorbent flaps for providing one or more liquid absorbing layers within the diaper. Each of the first and second liquid-absorbent flaps includes an at least partially hollow interior and an opening for allowing airflow into the hollow interior to facilitate drying.

In a further exemplary embodiment, a reusable diaper includes a forward waist portion, a rearward waist portion, and a crotch portion between the forward waist portion and the rearward waist portion. The diaper also includes at least one inner layer configured to be liquid-absorbent and at least one outer layer configured to be substantially liquid-impervious and coupled to the inner layer. A first liquid-absorbent flap has a fixed end portion coupled to the inner layer and a free end portion opposite the fixed end portion, which is not coupled to the reusable diaper. The first liquid-absorbent flap includes an at least partially hollow interior and an opening for allowing airflow into the hollow interior to facilitate drying of the first liquid-absorbent flap. A second liquid-absorbent flap has a fixed end portion coupled to the inner layer and a free end portion opposite the fixed end portion, which is not coupled to the reusable diaper. The second liquid-absorbent flap includes an at least partially hollow interior and an opening for allowing airflow into the hollow interior to facilitate drying of the second liquid-absorbent flap.

In another exemplary embodiment, a gender neutral reusable diaper generally includes at least one inner layer and at least one outer layer. At least one fluid-absorbing insert is coupled to the inner layer for use in absorbing fluids. The at least one inner layer is disposed generally between the at least one outer layer and the at least one fluid-absorbing insert. The at least one fluid-absorbing insert is adjustable relative to the at least one inner layer for accommodating use by a male and/or a female.

In another exemplary embodiment, a gender neutral reusable diaper generally includes a waist portion, at least one fluid-absorbing insert for use in absorbing fluids, and at least one liquid-resistant region disposed adjacent the waist portion between the waist portion and the at least one fluid-absorbing insert for resisting movement of fluid from the at least one fluid-absorbing insert to the waist portion. The at least one fluid-absorbing insert is adjustable relative to the waist portion by folding at least part of the at least one fluid-absorbing insert over itself at a desired location within the reusable diaper for accommodating use of the reusable diaper by a male and/or a female.

In another exemplary embodiment, a reusable diaper generally includes at least one inner layer, at least one outer layer, a forward waist portion, and a rearward waist portion. The at least one inner layer includes at least one forward liquid-resistant region disposed adjacent the forward waist portion for resisting movement of moisture through the at least one inner layer past the at least one forward liquid-resistant region. The at least one inner layer also includes at least one rearward liquid-resistant region disposed adjacent the rearward waist portion for resisting movement of moisture through the at least one inner layer past the at least one rearward liquid-resistant region.

Referring now to the drawings, FIGS. 1-5 illustrate an exemplary embodiment of an adjustable, gender neutral reusable diaper 2 embodying one or more aspects of the present disclosure. As will be described, the exemplary reusable diaper 2 may be adjusted as desired to accommodate use by a male and/or a female wearer. More particularly, a fluid-absorbing insert 4 of the reusable diaper 2 may be adjusted as desired to accommodate use by the male and/or female wearer. As will also be described, the reusable diaper 2 may also be adjusted (e.g., via adjustment system 46, etc.) to fit different sized male and/or female wearers, and/or may include liquid-resistant regions 6, 8 located to help resist undesired movement of moisture through the reusable diaper 2 (e.g., through forward and rearward waist portions 12, 14, etc.).

Figure 2:
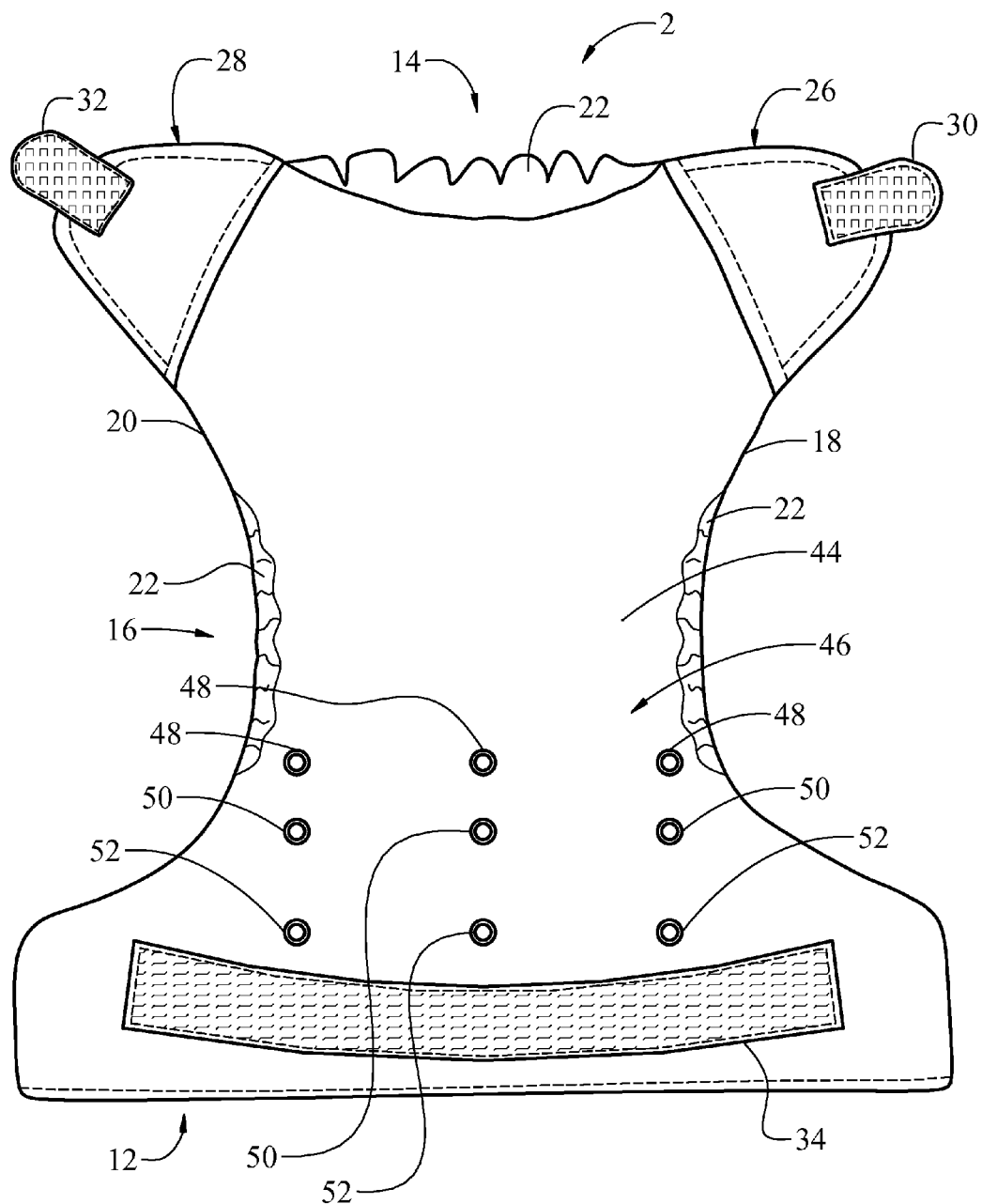
FIG. 2 is an outer view of the reusable diaper shown in FIG. 1.
Figure 3:
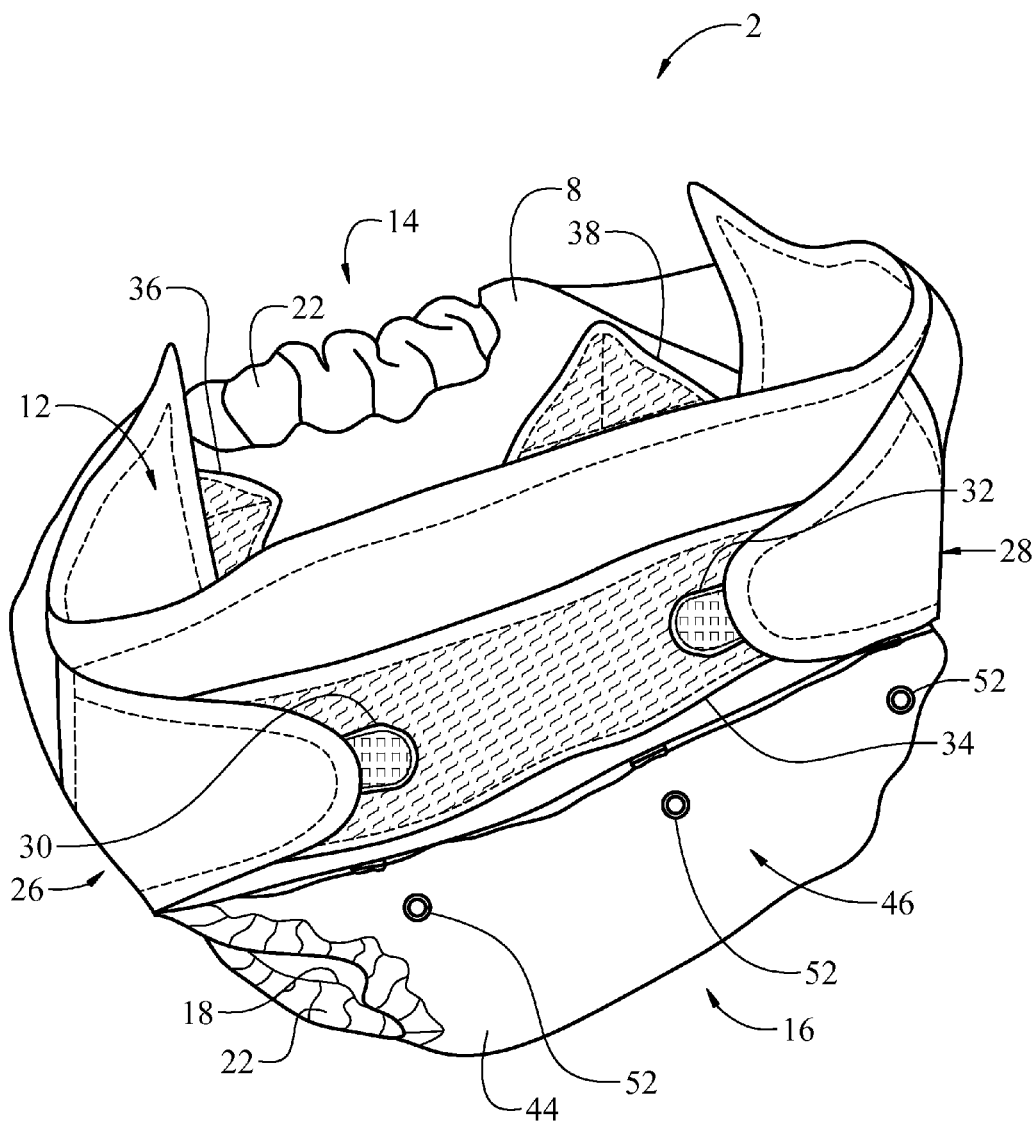
FIG. 3 is a perspective view of the reusable diaper of FIG. 1 shown secured in a generally closed position.

With reference to FIGS. 1-3, the reusable diaper 2 generally includes a forward waist portion 12, a rearward waist portion 14, and a crotch portion 16 disposed generally between the forward and rearward waist portions 12, 14. The contours of the forward and rearward waist portions 12, 14, together with the crotch portion 16, cooperatively define leg openings 18, 20 generally within the crotch portion 16 to accommodate a wearer's legs. In the illustrated embodiment, the leg openings 18, 20 include elastic 22 disposed adjacent the periphery of the leg openings 18, 20 for example, to help draw and hold the reusable diaper 2 securely against the wearer's legs, to inhibit leaking of fluids out of the reusable diaper 2 through the leg openings 18, 20, etc.

The rearward waist portion 14 of the reusable diaper 2 includes corner regions 26, 28 that may be releasably attached to the forward waist portion 12 to secure the reusable diaper 2 in a desired position (e.g., in a generally closed position as shown in FIG. 3, etc.). More particularly, tabs 30, 32 of the respective corner regions 26, 28 may be releasably attached (e.g., via corresponding hook-and-loop fasteners, etc.) to an elongate strip 34 of the forward waist portion 12 to secure the diaper 2 in the desired position (e.g., in the generally closed position, etc.). Elastic 22 is disposed along the rearward waist portion 14 to help ensure a snug fit of the reusable diaper 2 around a wearer's waist.

The tabs 30, 32 of the reusable diaper's corner regions 26, 28 may also be releasably attached to each other, for example, for closing the diaper 2 for storage, etc. For example, one of the tabs 30, 32 may have a forward surface with hook-and-loop fasteners that are releasably attachable to corresponding hook-and-loop fasteners on a rearward surface of the other tab 30, 32. The tabs 30, 32 may also be releasably attached to interior laundry closures 36, 38 of the rearward waist portion 14 (e.g., via corresponding hook-and-loop fasteners, etc.). This may, for example, help prevent or at least reduce snagging of the tabs 30, 32 when the reusable diaper 2 is being washed or laundered.

The corner regions 26, 28 and/or the tabs 30, 32 of the reusable diaper 2 may also be resiliently stretchable. This may allow for at least some adjustability of the diaper's functional waist size as defined by the forward and rearward waist portions 12, 14 when the rearward waist portion 14 is releasably attached to the forward waist portion 12 (e.g., via tabs 30, 32, etc.) in the generally closed position. For example, the corner regions 26, 28 may be formed from about 95% polyester and about 5% LYCRA® spandex material to allow them to stretch. However, the corner regions 26, 28 may be formed from other suitable materials within the scope of the present disclosure, and may or may not be resiliently stretchable.

Having resiliently elastic or stretchable corner regions 26, 28 (and/or tabs 30, 32 and/or elastic 22) with the ability to stretch can allow for tailoring of the diaper's functional waist size to the wearer's actual waist size. For example, the diaper's functional waist size may be selectively tailored for the wearer by stretching the corner regions 26, 28 (and/or tabs 30, 32 and or elastic 22), and then releasably attaching the tabs 30, 32 to the elongate strip 34 at desired attachment locations along the length of the elongate strip 34. In this exemplary manner, the diaper's functional waist size can be selectively adjusted, for example, to provide a relatively snug fit about the waist of the wearer (e.g., infant, toddler, adult, etc.), and preferably without being too uncomfortably tight about the wearer's thighs.

While the tabs 30, 32, the elongate strip 34, and the laundry closures 36, 38 of the reusable diaper 2 are each disclosed as including corresponding hook-and-loop fasteners, other suitable fasteners for coupling corresponding portions of the reusable diaper 2 together may be used within the scope of the present disclosure. For example, tabs, elongate strips, and/or laundry closures may include one or more of different hook-and-loop fastener arrangements (e.g., two or more spaced-apart discrete patches along the second waist portion instead of a single elongate strip, etc.), adhesives, snaps, buttons, clasps, various hook and loop closures, magnets, combinations thereof, etc. within the scope of the present disclosure.

With continued reference to FIGS. 1-3, the illustrated reusable diaper 2 also generally includes an inner layer 42 (FIG. 1) and an outer layer 44 (FIGS. 2 and 3) generally coupled to the inner layer 42 (e.g., seamed, stitched, melted, etc.). The inner layer 42 and the outer layer 44 may broadly be viewed as defining at least part of the forward and rearward waist portions 12, 14, and at least part of the crotch portion 16 of the reusable diaper 2. The inner layer 42 may be configured to absorb, wick, etc. moisture generally away, for example, from a diaper wearer, and may be formed of, for example, organic cotton, any suitable absorbent material, etc. The outer layer 44 may be configured to be substantially liquid-impervious to thereby resist wicking of moisture through the outer layer 44, and may be formed of polyester, water resistant material, coated materials, laminated materials, etc.

With particular reference to FIG. 1, the inner layer 42 includes two liquid-resistant regions 6, 8 that, for example, help resist wicking, movement, etc. of moisture through the inner layer 42 past the liquid-resistant regions 6, 8. A forward liquid-resistant region 6 is disposed adjacent the forward waist portion 12, and a rearward liquid-resistant region 8 is disposed adjacent the rearward waist portion 12, 14. The forward and rearward liquid-resistant regions 6, 8 each generally include a strip of material that may be coupled (e.g., seamed, stitched, melted, etc.), for example, to the inner layer 42 and/or to the outer layer 44. Each liquid-resistant region 6, 8 extends generally across a width of the reusable diaper's inner layer 42 to resist wicking, movement, etc. of moisture substantially along the width of the inner layer 42. As such, the forward liquid-resistant region 6 may be viewed as defining at least part of the forward waist portion 12, and the rearward liquid-resistant region 8 may be viewed as defining at least part of the rearward waist portion 14. It should be appreciated that a wide range of suitable materials, coatings, etc. may be used for the liquid-resistant regions 6, 8, including, for example, polyester materials, durable water repellant coatings, laminated fabrics, coated fabrics, etc.

As stated above, the two liquid-resistant regions 6, 8 of the illustrated reusable diaper 2 may help resist wicking, movement, etc. of moisture through the diaper 2 past the liquid-resistant regions 6, 8. In the illustrated embodiment, for example, the forward and rearward liquid-resistant regions 6, 8 are generally disposed adjacent the respective forward and rearward waist portions 12, 14, generally between the waist portions 12, 14 and the fluid-absorbing insert 4. This positioning may help resist wicking, movement, etc. of fluid from the fluid-absorbing insert 4, the inner layer 42, etc., through the forward and/or rearward waist portions 12 and/or 14 and to a shirt, blanket, article of bedding, etc. that may come into contact with the respective forward and/or rearward waist portions 12 and/or 14 (e.g., with an inner part of the forward and/or rearward waist portions 12 and/or 14, etc.). In other exemplary embodiments, reusable diapers may include inner layers having liquid-resistant regions shaped differently than disclosed herein; having liquid-resistant regions disposed, located, etc. differently than disclosed herein; having liquid-resistant regions with one or more separated parts; having less than or more than two liquid-resistant regions, etc. For example, in one exemplary embodiment, one or more liquid-resistant regions may be disposed adjacent one or more of a forward waist portion, a rearward waist portion, leg regions, etc. of a reusable diaper.

With particular reference now to FIGS. 2 and 3, an adjustment system 46 is provided along the outer layer 44 of the reusable diaper adjacent the forward waist portion 12 to allow for customization or adjustment to the reusable diaper's functional rise and/or crotch length. For example, the adjustment system 46 may allow for adjustment of the reusable diaper 2 such that the reusable diaper 2 may be adjusted to fit different sized wearers. This feature, in combination with the resiliently elastic or stretchable corner regions 26, 28 (and/or tabs 30, 32), elastic 22, etc.), may provide a generally one-size-fits all reusable diaper 2. This feature may also help create an even better and/or snugger fit to the diaper wearer (e.g., in combination with the resiliently elastic or stretchable corner regions 26, 28 (and/or tabs 30, 32), elastic 22, etc.). For example, the adjustment system 46 may help reduce the extent to which the crotch portion 16 hangs down below the wearer, and the corner region 26, 28 (and/or tabs 30, 32) and/or elastic 22 may help securely hold the reusable diaper 2 around a wearer's waist and/or legs. Adjustment systems may be located differently than disclosed herein (e.g., adjacent rearward waist portions, adjacent crotch portions, etc.) within the scope of the present disclosure.

The illustrated adjustment system 46 includes a three-by-three array of snaps 48, 50, 52, horizontally arranged and aligned in three rows and vertically arranged and aligned in three columns. A first row includes three spaced-apart male snaps 48; a second, or middle, row includes three spaced-apart female snaps 50; and a third row includes three-spaced apart female snaps 52. The male snaps 48 can be snapped together with either the female snaps 50 of the second row, or the female snaps 52 of the third row. For example, as shown in FIG. 3, the male snaps 48 of the first row can be snapped together with the corresponding female snaps 50 of the second row to thereby decrease the diaper's functional rise and/or crotch length. To decrease the diaper's functional rise and/or crotch length to an even greater extent, the male snaps 48 of the first row may instead be snapped together with the corresponding female snaps 52 of the third row.

The illustrated array of snaps 48, 50, 52 thus provide three different sizing configurations for the reusable diaper 2. The functional rise and/or crotch length of the reusable diaper 2 may be changed by selectively choosing whether to engage the male snaps 48 with the female snaps 50 of the second row, with the female snaps 52 of the third row, or by simply choosing to do neither. Thus, the exemplary three-by-three arrangement can eliminate or at least reduce the bulge in the middle front of the diaper 2 that typically occurs when there are only two columns of snaps due to the fabric bulging out between the two snaps. The three-by-three snap arrangement may help enable the diaper 2 to be more of a one-size fits all diaper 2.

The snaps 48, 50, 52 of the illustrated adjustment system 46 may be formed from a plastic material. Alternatively, the snaps 48, 50, 52 may be formed from other materials, for example lightweight and durable materials that can withstand repeated laundry cycles. In other exemplary embodiments, reusable diapers may include more or less than nine snaps and/or snaps arranged differently than illustrated herein. In addition, reusable diapers may include snaps in other arrangements than disclosed herein, for example, two rows of male snaps with only one row of female snaps, or rows having both male and female snaps. Additional exemplary embodiments include reusable diapers with more or less than three rows of snap members and/or more or less than three columns of snap members.

While the illustrated adjustment system 46 includes an array of snaps 48, 50, 52, other exemplary adjustment systems or fasteners means may be used within the scope of the present disclosure. For example, such other adjustment systems or fastener means may include adhesives, buttons, clasps, various hook and loop closures, magnets, elastic straps, adjustable straps, combinations thereof, etc.

Figure 4:
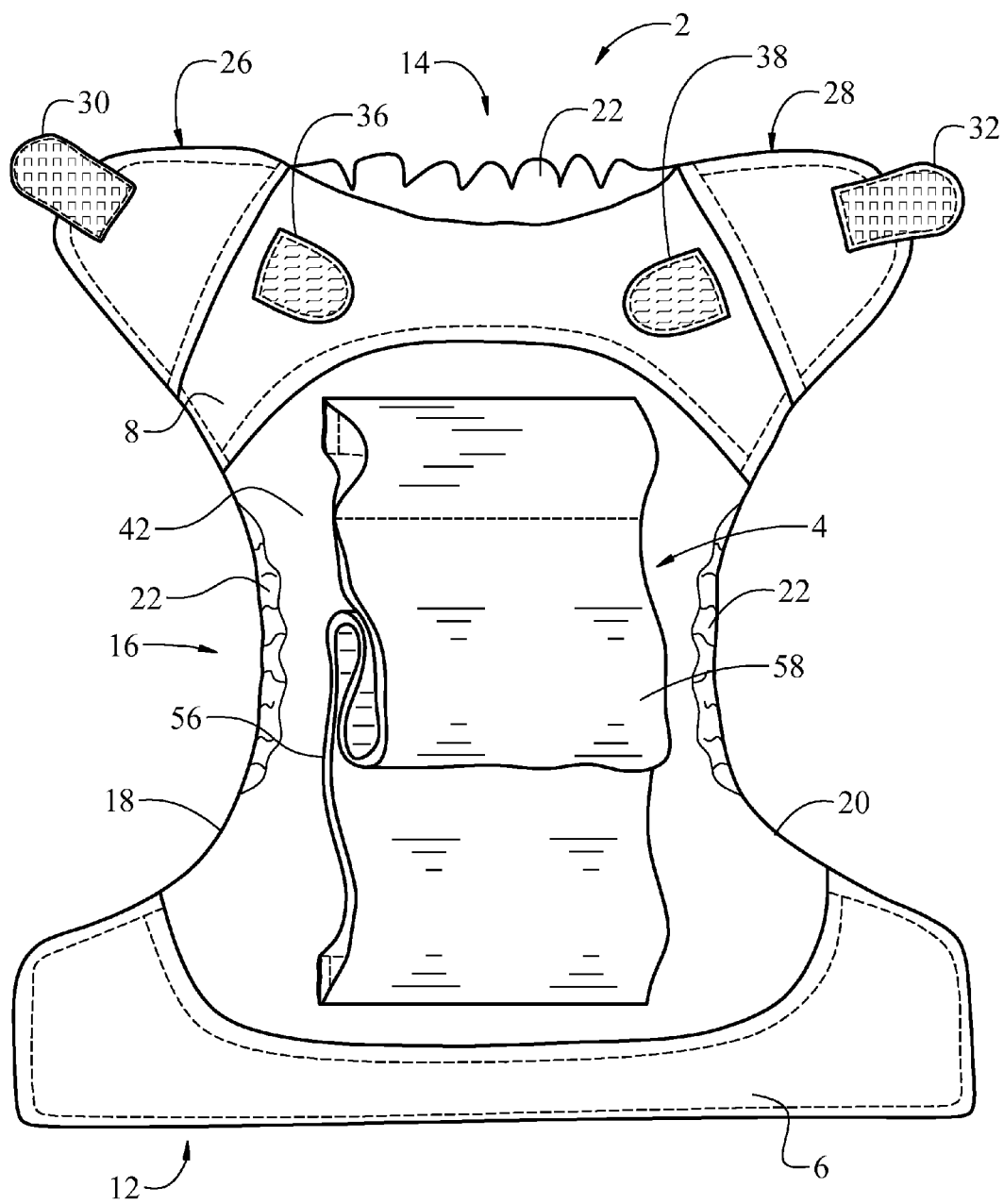
FIG. 4 is a view similar to FIG. 1 with the fluid-absorbing insert shown at least partly folded over itself in position for accommodating use by a female wearer.
Figure 5:
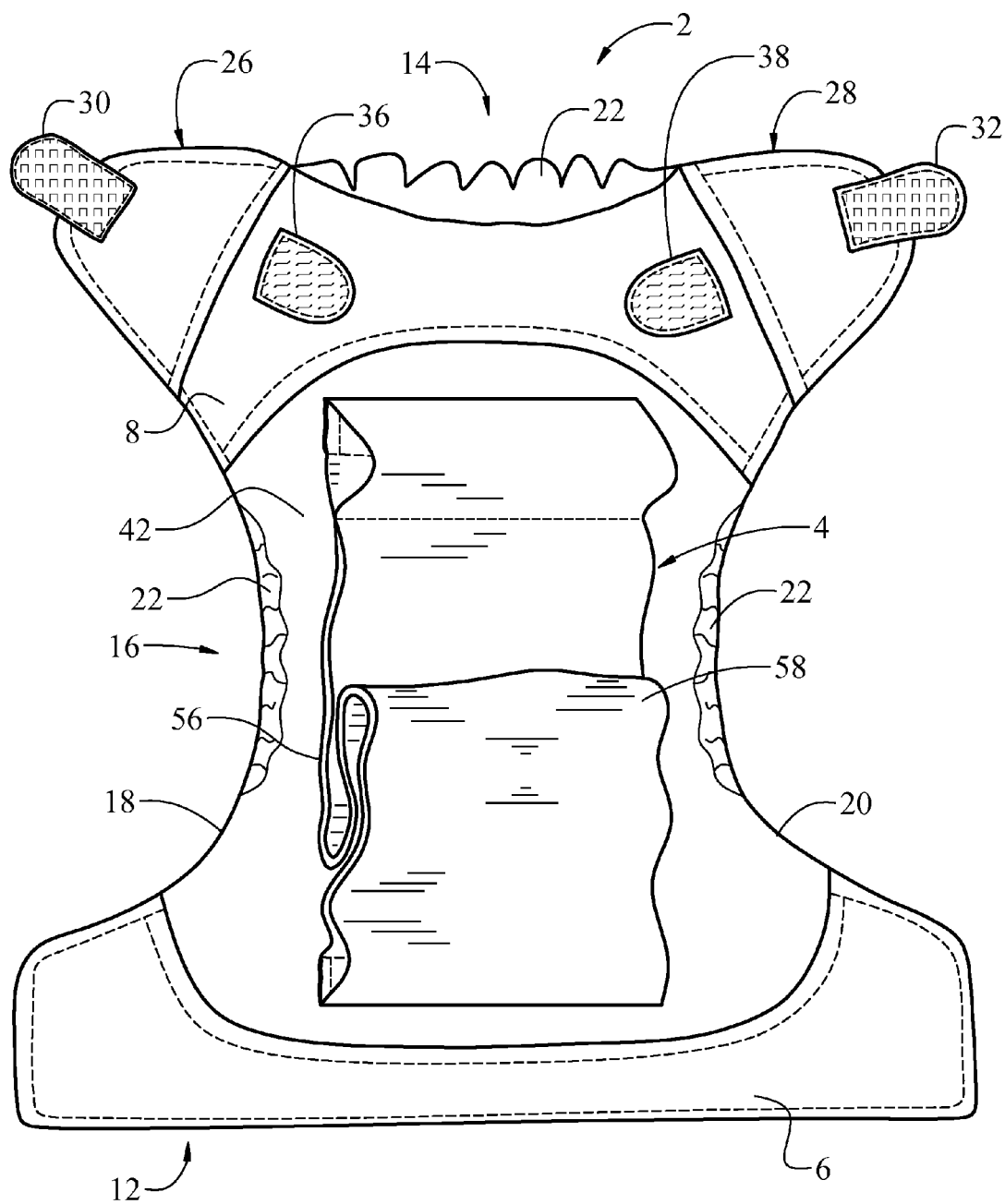
FIG. 5 is a view similar to FIG. 1 with the fluid-absorbing insert shown at least partly folded over itself in position for accommodating use by a male wearer.

With reference now to FIGS. 1, 4, and 5, the adjustable fluid-absorbing insert 4 of the reusable diaper 2 will be described. The fluid-absorbing insert 4 is positioned within the reusable diaper 2 to absorb liquids within the reusable diaper 2, for example liquids discharged into the reusable diaper 2 by a wearer, etc. In the illustrated embodiment, the fluid-absorbing insert 4 is coupled to the reusable diaper's inner layer 42 such that the inner layer 42 is disposed generally between the outer layer 44 and the fluid-absorbing insert 4. In this position, the fluid-absorbing insert 4 may absorb liquids within the reusable diaper 2 (e.g., fluids discharged by the diaper's wearer), and the inner layer 42 may absorb liquids within the reusable diaper 2 that, for example, move outwardly past the fluid-absorbing insert 4, soak through the fluid-absorbing insert 4, etc.

As best shown in FIG. 1, the illustrated fluid-absorbing insert 4 includes two individual and separate (and at least partly spaced apart) layers 56, 58 of material. The two layers 56, 58 are each stitched to the reusable diaper's inner layer 42 at two locations: a first location adjacent the forward waist portion 12 and a second location adjacent the rearward waist portion 14. For example, free ends of each of the layers 56, 58 may be overlapped and then stitched to the inner layer 42. The two layers 56, 58 may further be stitched together at a third location adjacent the rearward waist portion 14. This may help hold the two layers 56, 58 in position together, and/or may help with sizing and positioning the two layers 56, 58 as desired. In other exemplary embodiments, reusable diapers may include fluid-absorbing inserts having more than or less than two layers of material. In addition, fluid-absorbing insert layers may be coupled together differently and/or may be coupled to reusable diapers differently (e.g., to inner layers of the reusable diapers at locations other than disclosed herein (e.g., adjacent crotch portions, etc.)) within the scope of the present disclosure. Moreover, a single piece of material may be used to form fluid-absorbing insert layers.

The layers 56, 58 of the illustrated fluid-absorbing insert 4 are formed from organic cotton material. However, the fluid absorbing insert layers 56, 58 may comprise in part or in whole one or more of microfibers, hemp, hydrocolloid materials, other suitable absorbent materials, combinations thereof, etc. within the scope of the present disclosure. Materials other than organic materials may also be used.

As shown in FIGS. 4 and 5, the layers 56, 58 of the fluid-absorbing insert 4 are together adjustable relative to the reusable diaper's inner layer 42, for example, for accommodating use of the reusable diaper 2 either by a female wearer (e.g., FIG. 4, etc.) or a male wearer (e.g., FIG. 5, etc.). The fluid-absorbing insert layers 56, 58 are thus also viewed as adjustable relative to the reusable diaper's forward waist portion 12 and rearward waist portion 14, at locations generally between the forward waist portion 12 and rearward waist portion 14. Such adjustability may allow for positioning the layers 56, 58 of the fluid-absorbing insert 4 as desired to ensure that fluids, for example fluids discharged into the reusable diaper 2 by a wearer, are substantially absorbed by the fluid-absorbing insert 4. Thus, this may help inhibit fluids from pooling and/or leaking out of the reusable diaper 2 onto the wearer's clothes, body, bedding, toys, furniture, etc.

To adjust the fluid-absorbing insert 4, the layers 56, 58 are folded, bulked up, gathered, etc. over themselves to provide an overlapped, layered, built up, etc. region at the desired location (e.g., at the desired location to accommodate the female or male wearer, etc.). This overlapped region may provide additional liquid absorbing capacity (e.g., additional absorbing material, layers, etc.) at the desired location within the reusable diaper 2, and thus help inhibit undesired leaks. As shown in FIG. 4, for example, the fluid-absorbing insert layers 56, 58 can be folded over themselves adjacent the reusable diaper's crotch portion 16 to accommodate use by a female wearer. Here, the fluid-absorbing insert layers are overlapped at a typical central location to absorb fluids discharged by the female wearer. And as shown in FIG. 5, for example, the fluid-absorbing insert layers 56, 58 can be folded over themselves adjacent the reusable diaper's forward waist portion 12 to accommodate use by a male wearer. Here, the fluid-absorbing insert layers 56, 58 are overlapped at a typical forward location to absorb fluids discharged by the male wearer.

It should now be appreciated that the reusable diaper 2 may be put on either male or female wearers having varying, differing, etc. body sizes, waist sizes, etc. The adjustment system may first be adjusted to accommodate the body size of the wearer. The reusable diaper may then be put on the wearer with the fluid-absorbing insert 4 (as well as part of the inner layer 42) positioned against the skin of the wearer. The fluid-absorbing insert 4 may be folded, bulked up, etc. at the desired location to accommodate a male or female wearer. The first and second corner regions 26, 28 (e.g., the tabs 30, 32) of the rearward waist portion 14 may next be secured to the elongate strip 34 of the forward waist portion 12 to secure the reusable diaper 2 on the wearer. In this position, the fluid-absorbing insert 4 and/or the inner layer 42 can absorb moisture from the wearer (e.g., bodily discharge, urine, sweat, etc.). When the fluid-absorbing insert 4 becomes saturated, the reusable diaper 2 may be removed from the wearer and washed or laundered. After the reusable diaper 2 (and fluid-absorbing insert 4) has been satisfactorily washed and dried, the reusable diaper 2 may be reused.

In other exemplary embodiments, the diaper 2 may be provided with overlapping liquid-absorbent flaps, tongues, pads, liners, or layers similar to the flaps 156, 158 shown in FIGS. 6-13 and described below in addition to, or as an alternative to the fluid-absorbing insert or pad 4 and layers 56, 58. In addition, it is noted that other individual elements or features of a particular embodiment disclosed herein are generally not limited to that particular embodiment, but, where applicable, are interchangeable and can be used in a selected embodiment, even if not specifically shown or described.

In still other exemplary embodiments, reusable diapers may include fluid-absorbing inserts, pads, layers, etc. releasably coupled to the reusable diapers. For example, snaps, adhesives, buttons, clasps, various hook and loop closures, magnets, elastic straps, adjustable straps, combinations thereof, etc. may be used to couple the fluid-absorbing inserts to the reusable diapers. Here, when the fluid-absorbing inserts become saturated, soiled, etc., they may be washed and/or laundered either together with the reusable diaper or separate therefrom. If laundered separately, one the fluid-absorbing inserts and the reusable diapers are washed and dried, the fluid-absorbing inserts may be repositioned within and re-coupled to the reusable diapers for further use.

FIGS. 6-13 illustrate another exemplary embodiment of a reusable diaper (indicated generally at 102) embodying one or more aspects of the present disclosure. As shown, the reusable diaper 102 includes liquid-absorbent flaps, tongues, pads, liners, or layers 156, 158 that are positionable in an overlapping manner along the crotch portion 116 of the diaper 102, so as to form or define a liquid or moisture absorbent inner portion of the diaper 102. The overlapped flaps 156, 158 are also slidable relative to each other for sizeability and/or for accommodating changes to the diaper's functional rise and/or crotch length such as when adjusting or tailoring the diaper size to the wearer (e.g., infant, toddler, adult, etc.).

Figure 7:
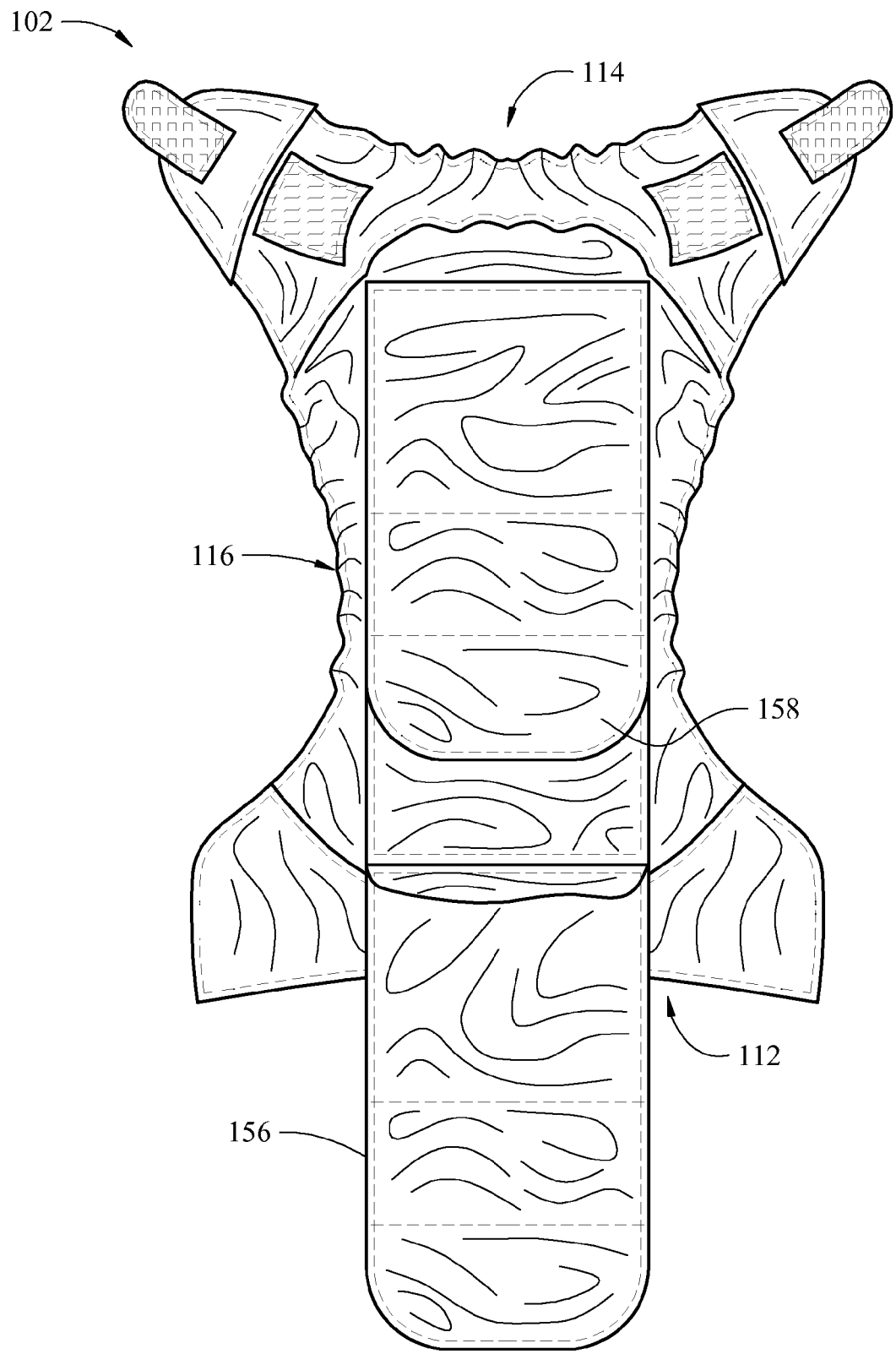
FIG. 7 is a view similar to FIG. 6 with the rearward flap shown along the crotch portion of the diaper.
Figure 8:
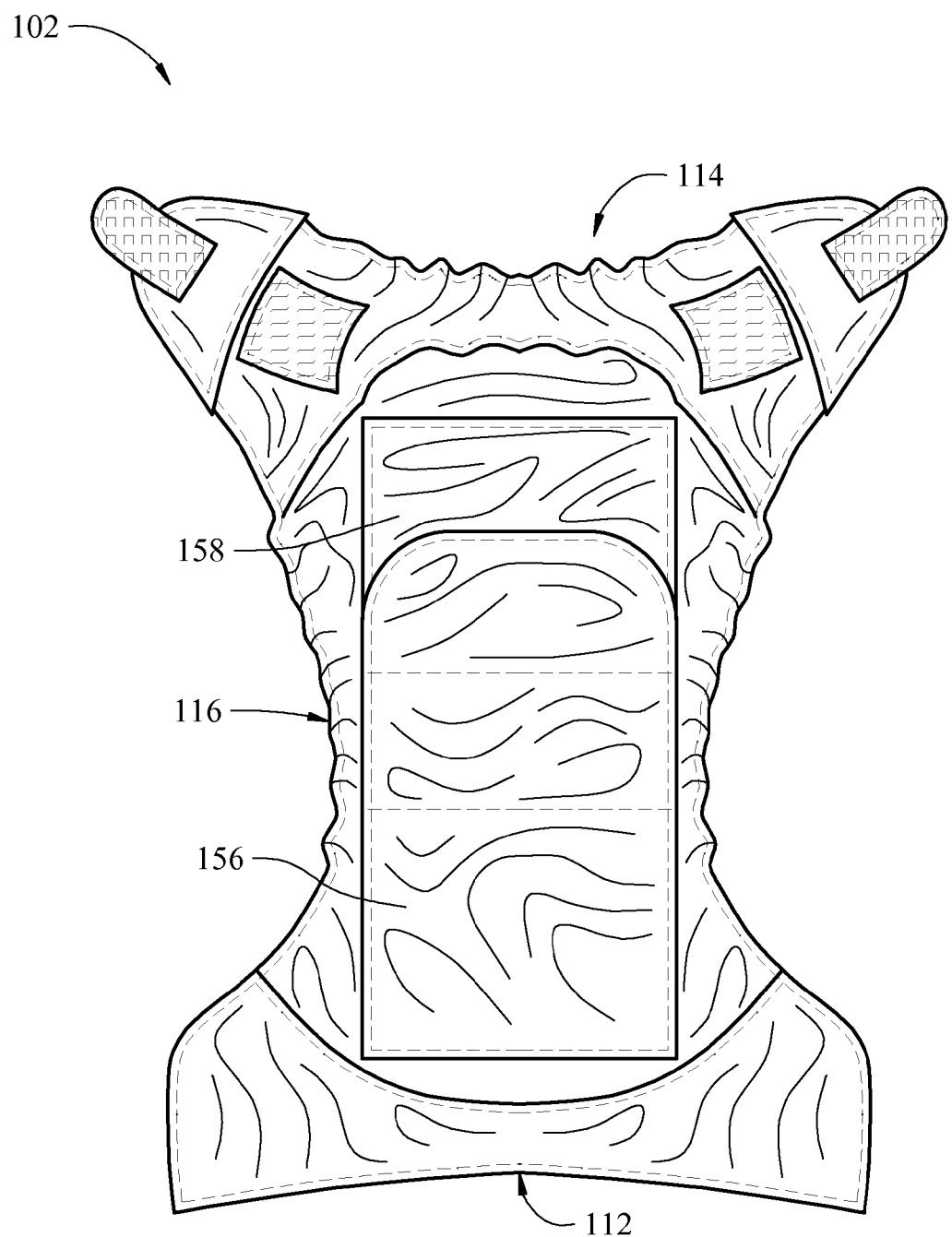
FIG. 8 is a view similar to FIG. 7 with the forward flap shown on top of and overlapping the rearward flap.
Figure 9:
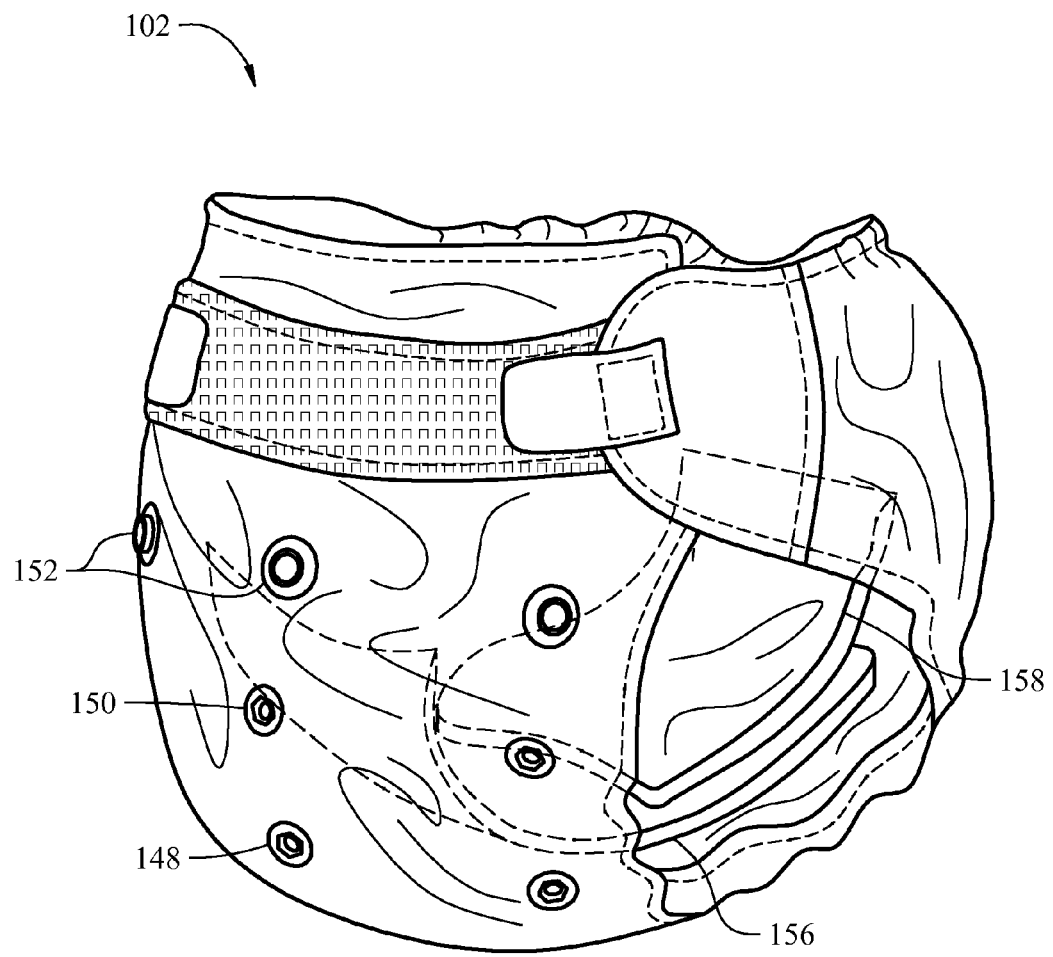
FIG. 9 is a perspective view of the reusable diaper of FIG. 8 shown secured in a generally closed position without any of the snap members along the diaper's forward portion snapped together.
Figure 10:
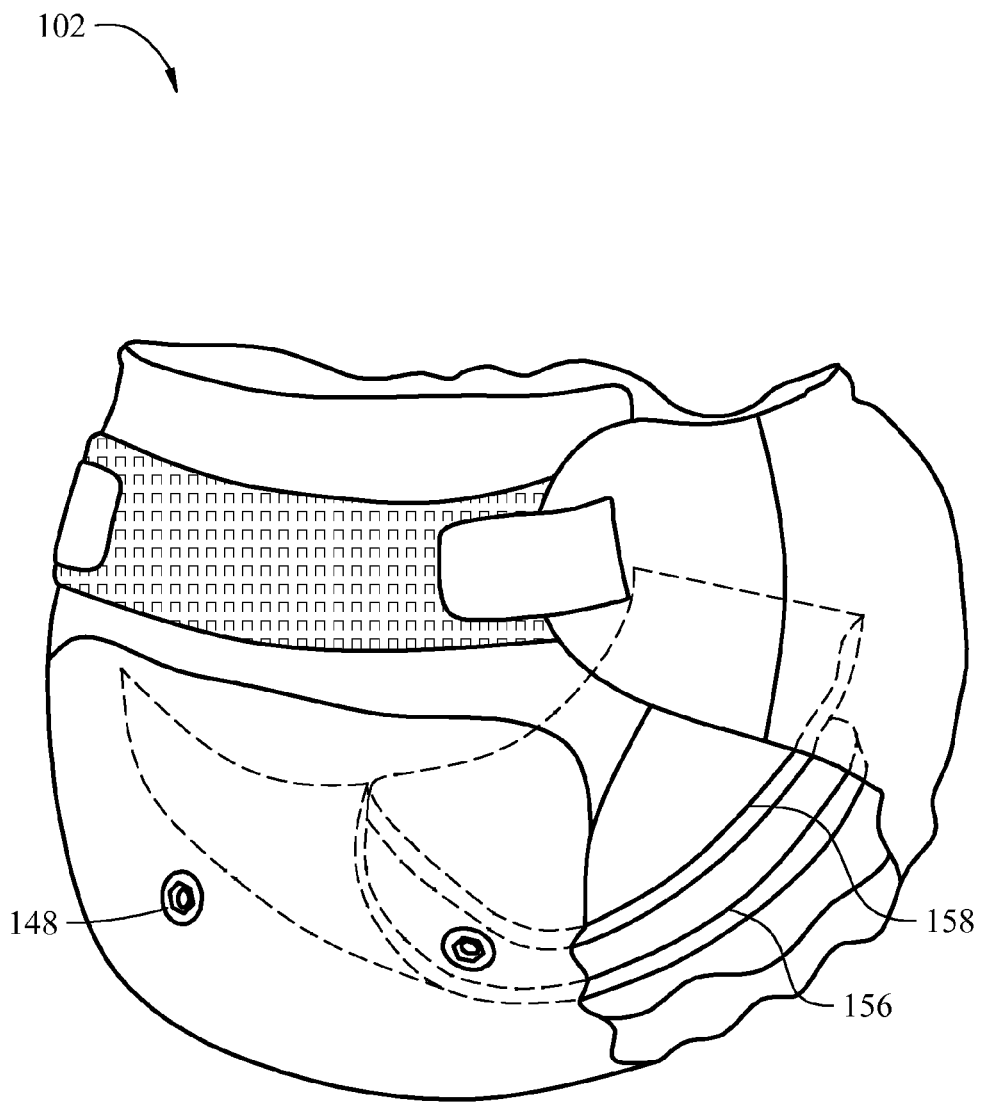
FIG. 10 is another perspective view of the reusable diaper shown in FIG. 9 wherein the top and middle rows of snap members along the diaper's forward portion have been snapped together, which reduces the diaper's functional rise or crotch length and also overlappingly slides the upward flap over or along the lower flap as compared to FIG. 9.
Figure 11:
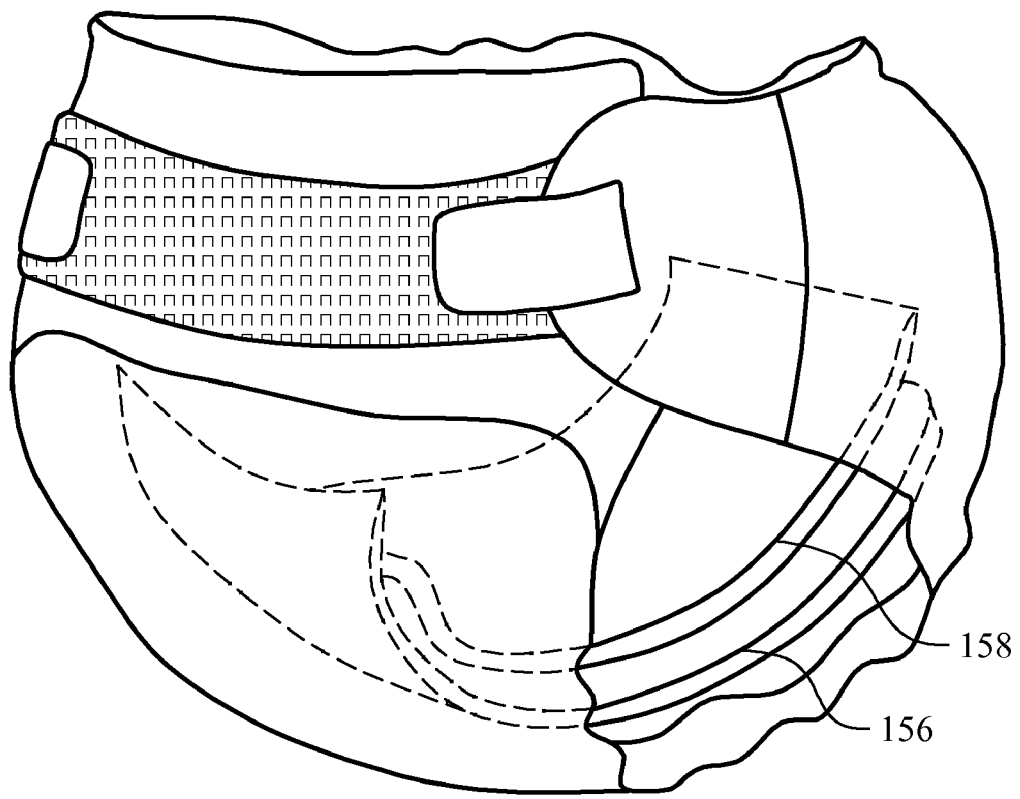
FIG. 11 is another perspective view of the reusable diaper shown in FIG. 10 wherein the top and bottom rows of snap members along the diaper's forward portion have been snapped together, which further reduces the diaper's functional rise or crotch length and also further overlappingly slides the upper flap over the rearward flap as compared to FIG. 10.

In use, one of the flaps 156 or 158 may first be positioned (e.g., folded downwardly, etc.) so that it lies along the diaper's crotch portion 116 generally between the diaper's forward and rearward waist portions 112, 114. Then, the other flap 156 or 158 may be positioned (e.g., folded downwardly, etc.) to overlap the flap 156 or 158 that is lying along the diaper's crotch portion 116. As shown by a comparison of FIGS. 6-8, this illustrated example first positions the rearward flap 158 along the crotch portion 116 (FIG. 7), and then the forward flap 156 is positioned to overlap the rearward flap 158 (FIG. 8). Conversely, FIGS. 9-11 illustrate the forward flap 156 being overlapped by the rearward flap 158.

The other features of the diaper 102 may be substantially the same as or similar to the corresponding features of the diaper 2 shown in FIGS. 1-5 and described above. For example, the diaper 102 may include features substantially the same as or similar to the following features of diaper 2, e.g., liquid resistant regions 6, 8, leg openings 18, 20, elastic 22 along the rearward waist portion 14, stretchable corner regions 26, 28, tabs 30, 32, an elongate strip 34 along the forward waist portion 12, interior laundry closures 36, 38, inner and outer layers 42, 44, and the adjustment system 46 with snaps 48, 50, 52. Alternative embodiments of the diaper 102 may include the flaps 156 and 158 and the fluid-absorbing insert 4 having two individual and separate layers 56, 58 as disclosed above for diaper 2. In further alternative embodiments, the diaper 102 may include features configured differently than the corresponding features of diaper 2.

In this illustrated example embodiment, the diaper 102 has a single, unitary construction as its various features are not removable or completely separable from the diaper 102. Instead, the various components of the diaper 102 are coupled together, such as by stitching, sewing, adhesives, etc. In other embodiments, however, one or more features of the diaper 102 may be configured to be removably attachable to and completely separable from the diaper 102.

Figure 6:
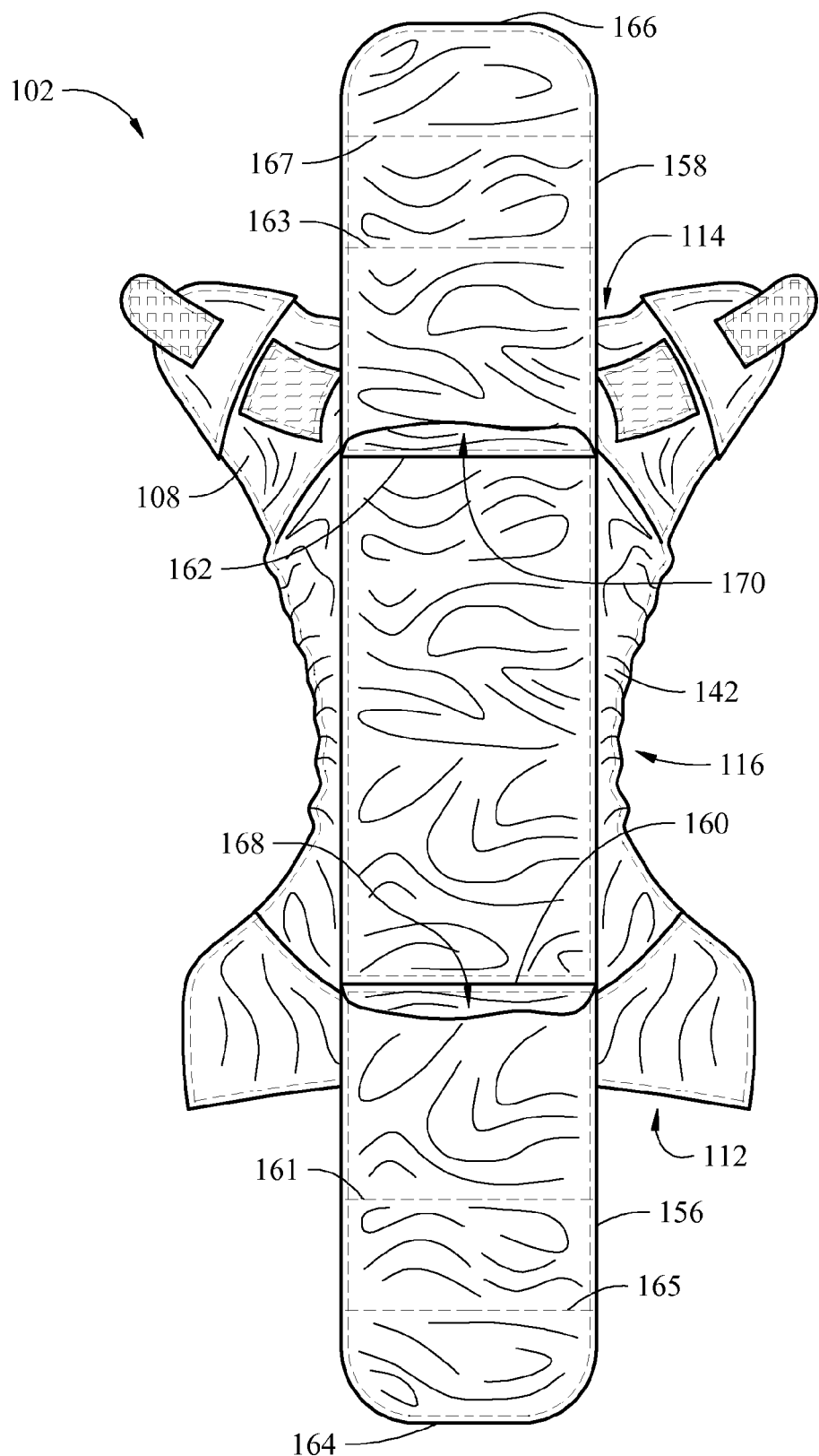
FIG. 6 is an inner view of an exemplary embodiment of a reusable diaper having overlapping liquid-absorbent flaps or tongues that are positionable in an overlapping manner and slidable relative to each other for sizeability and/or for accommodating changes to the diaper's functional rise and/or crotch length.
Figure 13:
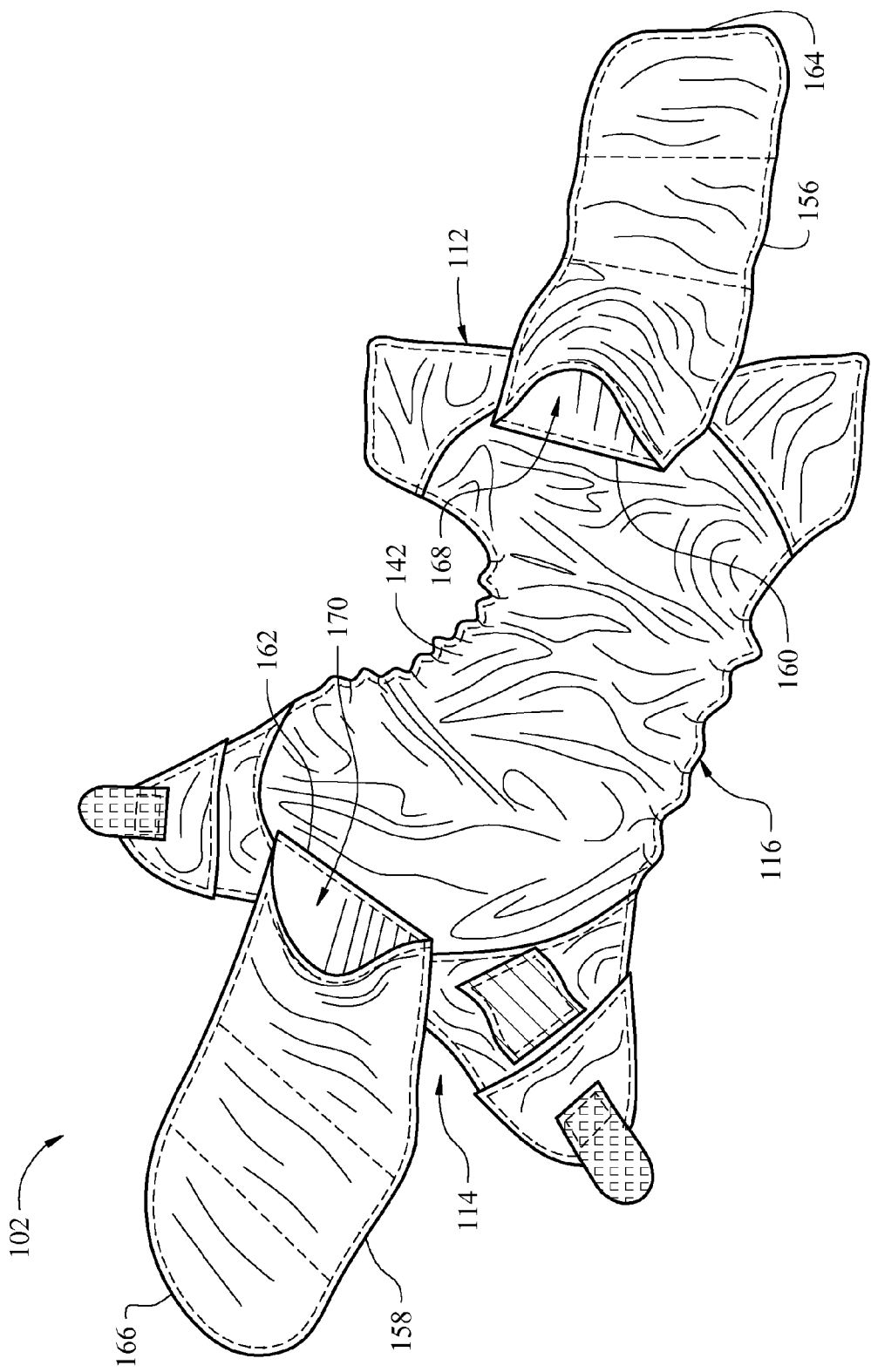
FIG. 13 is a perspective view of the reusable diaper shown in FIG. 6.

With continued reference to FIGS. 6 and 13, each flap 156, 158 includes a fixed end portion 160 and 162, respectively, coupled (e.g., stitched, etc.) to the inner layer 142 of the diaper 102. Each flap 156, 158 includes a free end portion 164, 166, respectively, that is opposite its fixed end portion 160, 162. The free end portions 164, 166 are not attached (e.g., stitched, etc.) to the reusable diaper 102, such that each flap 156, 158 is thus hingedly or pivotably movable relative to the inner layer 142 about its fixed end portion 160, 162 as shown by a comparison of FIGS. 6 through 8.

In this example embodiment, the flaps 156, 158 are shown stitched to the inner layer 142 such that the fixed end portion 160 of the first or forward flap 156 is closer to the forward liquid resistant region 106 than it is to the rearward liquid resistant region 108 and such that the fixed end portion 162 of the second or rearward flap 158 is closer to the rearward liquid resistant region 108 than it is to the forward liquid resistant region 106. In alternative embodiments, the flaps 156, 158 may be coupled differently to a reusable diaper, such as via other means besides stitching and/or coupled to the inner layer of the reusable diaper at locations other than disclosed herein (e.g., adjacent crotch portions, etc.). In addition, the flaps 156, 158 are illustrated with about the same length and such that the flaps 156, 158 overlap (FIG. 8) even when the diaper 102 is lying flat and opened. In other embodiments, the flap 156 may have a different configuration (e.g., shape, size, etc.) than the flap 158. Additionally, or alternatively, the flaps 156, 158 may be sized such that they do not overlap when the diaper is lying flat and open and/or such that they do not overlap when the diaper is merely closed without any reduced functional rise or crotch length.

In this illustrated embodiment of FIGS. 6 and 13, each flap 156, 158 includes an at least partially hollow interior and an opening 168, 170, respectively, for allowing airflow into the hollow interior to facilitate drying. Each flap 156, 158 includes first and a second liners coupled (e.g., stitched, etc.) together to form a pocket defining the hollow interior and opening, which pocket permits exposure of the hollow interior between the first and second liners for drying. In this example, the first and second liners of each flap 156, 158 are stitched together (as shown by the dashed lines in FIGS. 6 and 13) along three edges with a fourth edge of the first liner being stitched to the inner layer 142 of the diaper 102. With this configuration, a pocket is thereby formed having the opening 168, 170 defined along and between the fourth edges of the first and second liners which are not stitched to each other. Alternative embodiments may include flaps having liners coupled together via other means besides stitching and/or liners that are coupled to each other at different locations than their three edges as shown in FIGS. 6 and 13. Moreover, a single piece of material may be used to the flap 156 and/or flap 158 in other embodiments.

The liquid-absorbent flaps 156, 158 may be formed from a wide variety of materials that are configured to absorb and store liquids therein. By way of example, the liquid-absorbent flaps 156, 158 may comprise one or more of microfibers, hemp, hydrocolloid materials, or any other suitable material configured to absorb and store liquids therein. In some exemplary embodiments, the liquid-absorbent flaps 156, 158 are formed from one or more of organic cotton material, microfiber terry, and/or suede cloth.

The flaps 156, 158 are positionable in an overlapping manner such that they are slidable relatively along each other. The relative sliding of the flaps 156, 158 provides further sizeability by accommodating for changes to the functional rise and/or crotch length of the reusable diaper 102 via the selective attachment of the snaps 148 with either the second or third row of snaps 150 or 152 or by opting not to attach the snaps 148 to either row of snaps 150, 152.

The flaps 156, 158 are able to slide relatively along and towards each other when the diaper's functional rise and/or crotch length is reduced for a smaller diaper wearer. With this sliding movement, the upper flap will overlap the lower flap to a greater extent. This allows the overlapping flaps 156, 158 to remain disposed along the crotch portion 116 without bunching up despite the shorter crotch length, which improves user comfort. The sliding movement and overlap allows the flaps 156, 158 to retain a configuration (e.g., relatively flat, contoured, curved, etc.) that corresponds to the configuration (e.g., shape, etc.) of the crotch portion 116 as shown by a comparison of FIGS. 9-11.

Conversely, the flaps 156, 158 are also able to slide opposing each other when the diaper's functional rise and/or crotch length is increased for a larger diaper wearer. With this relative sliding movement, the upper flap will overlap the lower flap to a lesser extent if at all. Also, the sliding movement of the flaps 156, 158 in opposite directions away from each other also accommodates for the increased functional rise and/or crotch length by allowing the interior portions of the diaper 102 to which the flaps 156, 158 are coupled to be positioned farther apart from each other.

In addition to being overlappable and slidable relative to each other, the overlappable flaps, tongues, or liquid-absorbent layers of a reusable diaper may also be foldable. In such exemplary embodiments, either or both flaps may be folded over itself to selectively provide one or more additional liquid absorbing layers towards or adjacent the forward waist portion, rearward portion, and/or crotch portion depending on whether the wearer is male or female so as to provide desired protection to accommodate the male or female wearer.

Figure 12:
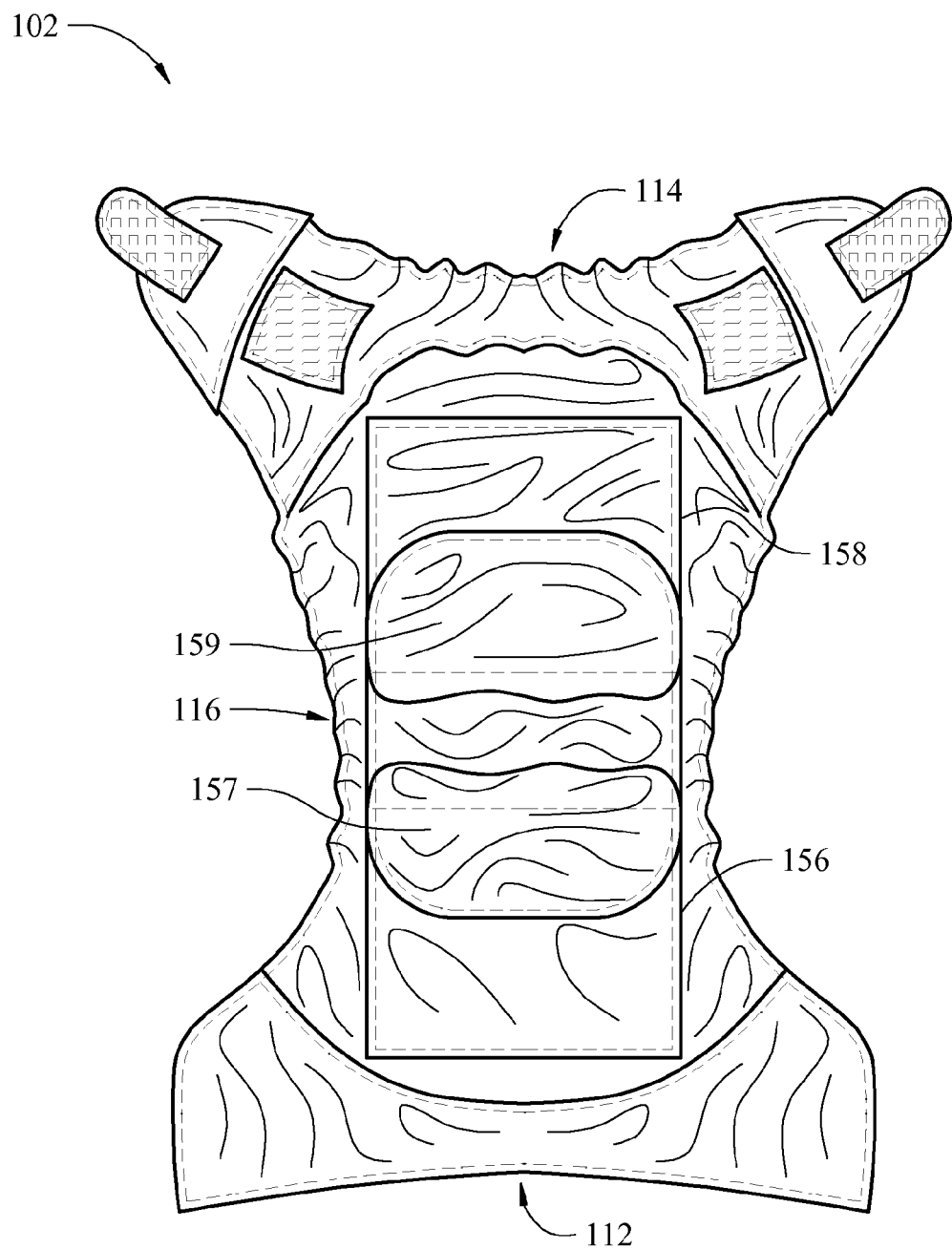
FIG. 12 is a view similar to FIG. 6 with each of the forward and rearward flap shown at least partly folded itself for creating additional liquid absorbing layers.

For example, FIG. 12 illustrates the diaper 102 with each of the forward and rearward flaps 156, 158 folded over itself to thereby provide additional liquid absorbing layers 157, 159, respectively, adjacent or within the crotch portion 116 of the diaper 102. As shown, the additional liquid absorbing layer 157 is closer to the forward portion 112 than it is to the rearward portion 114, whereas the liquid absorbing layer 159 is closer to the rearward portion 114 than it is to the forward portion 112. In FIG. 12, the flaps 156, 158 are illustrated after being folded once along their respective fold lines 161, 163.

But the flaps 156, 158 may also or instead be folded along their respective fold lines 165, 167. For example, either or both flaps 156, 158 may be folded twice to create further liquid absorbing layers. In which case, either or both flaps 156, 158 may be first folded along their respective fold lines 161, 163 and then folded a second time along their respective fold lines 165, 167. As shown by FIGS. 6 through 8, however, this foldability of the flaps 156, 158 is optional as the flaps 156, 158 may be merely overlapped without folding any portions of the flaps 156, 158. Moreover, other exemplary embodiments may include flaps that are overlappable and slidable relative to each other, but which are not foldable or readily foldable.

The snap members 148, 150, 152 of diaper 102 may be substantially the same as or similar to the snap members 48, 50, 52 of reusable diaper 2 described above. As before with diaper 2, the diaper 102 is illustrated with a three-by-three array of snap members such that the snap members are horizontally arranged and aligned in the three rows and vertically arranged and aligned in the three columns. Advantageously, having at least three columns may provide a more snug and precise fit to the diaper wearer, for example, by reducing the extent to which the crotch portion hangs down below the wearer. The three-by-three arrangement can eliminate or at least reduce the bulge in the middle front of the diaper that typically occurs when there are only two columns of snaps due to the fabric bulging out between the two snaps. The three-by-three snap arrangement may enable the diaper to be more of a one-size fits all cloth diaper.

In alternative embodiments, the reusable diaper 102 may include more or less snap options and/or snap members in other arrangements than what is shown in FIG. 9. For example, another embodiment may include two rows of male snap members with only one row of female snap members. As another example embodiment, a diaper may include a row having both male and female snap members. Additional examples include diapers having more or less than three rows of snap members and/or more or less than three columns of snap members. Still further embodiments may include a wide range of other suitable fastening means or fastening systems besides snaps, such as adhesives, buttons, clasps, Velcro® hook and loop closures, magnets, elastic straps, adjustable straps, combinations thereof, etc.

Other aspects of the present disclosure relate to methods, such as methods of using any one or more of the various reusable diapers (e.g., 2, 102, etc.) disclosed herein. In an exemplary embodiment, a method generally includes positioning first and second flaps in an overlapping manner along a crotch portion of the diaper. The method may also include increasing the crotch length or functional rise of the diaper such that the overlapping first and second flaps slide relative to each other in opposite directions. The method may instead include reducing the crotch length or functional rise of the diaper such that the overlapping first and second flaps slide relatively toward each other.

Numerical dimensions and values are provided herein for illustrative purposes only. The particular dimensions and values provided are not intended to limit the scope of the present disclosure.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The disclosure herein of particular values and particular ranges of values for given parameters are not exclusive of other values and ranges of values that may be useful in one or more of the examples disclosed herein. Moreover, it is envisioned that any two particular values for a specific parameter stated herein may define the endpoints of a range of values that may be suitable for the given parameter. The disclosure of a first value and a second value for a given parameter can be interpreted as disclosing that any value between the first and second values could also be employed for the given parameter. Similarly, it is envisioned that disclosure of two or more ranges of values for a parameter (whether such ranges are nested, overlapping or distinct) subsume all possible combination of ranges for the value that might be claimed using endpoints of the disclosed ranges.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A reusable diaper comprising:
   a forward waist portion;
   a rearward waist portion;
   a crotch portion between the forward waist portion and the rearward waist portion; and
   first and second liquid-absorbent flaps each having a fixed end portion coupled to the diaper and a free end portion opposite the fixed end portion, which is not coupled to the reusable diaper,
   the free end portion of the first liquid-absorbent flap at least partially overlapping the free end portion of the second liquid-absorbent flap along the crotch portion,
   wherein the reusable diaper is configured to define a plurality of different functional rises;
   wherein the first and second liquid-absorbent flaps are slidable relative to one another to accommodate the plurality of functional rises;
   wherein the second liquid-absorbent flap extends from its fixed end portion towards the fixed end portion of the first liquid-absorbent flap, but not beyond the fixed end portion of the first liquid-absorbent flap when the second liquid-absorbent flap is unfolded and the reusable diaper defines a first one of the plurality of functional rises and when the second liquid-absorbent flap is unfolded and the reusable diaper defines a second one of the plurality of functional rises.

2. The reusable diaper of claim 1, wherein:
   the diaper includes a plurality of connector members spaced apart from one another along a forward portion of the diaper, the connector members selectively engagable to change between the plurality of functional rises of the reusable diaper.

3. The reusable diaper of claim 1, wherein each of the first and second liquid-absorbent flaps includes an at least partially hollow interior and an opening for allowing airflow into the at least partially hollow interior to facilitate drying.

4. The reusable diaper of claim 3, wherein each of the first and second liquid-absorbent flaps includes a first liner and a second liner coupled together to form a pocket defining the at least partially hollow interior and the opening.

5. The reusable diaper of claim 4, wherein the first and second liners are formed from one or more of organic cotton material, microfiber terry, and/or suede cloth; and
   wherein at least one of the first and second liquid-absorbent flaps includes at least one fold line between the fixed end portion and the free end portion thereof.

6. The reusable diaper of claim 4, wherein the first liquid-absorbent flap includes at least one fold line between the fixed end portion and the free end portion, the fold line at least partially defines the pocket.

7. The reusable diaper of claim 6, wherein the first liner of the first liquid-absorbent flap is coupled to the second liner of the first liquid-absorbent flap along the fold line.

8. The reusable diaper of claim 1, wherein the forward waist portion, the rearward waist portion, and the crotch portion are at least partially defined by:
   at least one inner layer configured to be liquid-absorbent; and
   at least one outer layer configured to be substantially liquid-impervious, and coupled to the inner layer; and
   wherein the fixed end portions of the first and second liquid-absorbent flaps are coupled to the inner layer.

9. The reusable diaper of claim 8, wherein the first and second liquid-absorbent flaps are coupled to the inner layer by stitches.

10. A reusable diaper comprising:
    a forward waist portion;
    a rearward waist portion;
    a crotch portion between the forward waist portion and the rearward waist portion;
    a first liquid-absorbent flap having a free end portion and an end portion fixedly coupled to one of the crotch portion and the forward waist portion; and
    a second liquid-absorbent flap having a free end portion and an end portion fixedly coupled to one of the crotch portion and the rearward waist portion;
    the free end portions of the first and second liquid-absorbent flaps slidable relative to one another; and
    wherein the second liquid-absorbent flap defines a length, such that the second liquid-absorbent flap extends toward the forward waist portion, but not beyond the fixed end portion of the first liquid-absorbent flap, when the second liquid-absorbent flap is unfolded and the reusable diaper defines at least one functional rise.

11. The reusable diaper of claim 10, wherein the first and second liquid-absorbent flaps are overlappingly slidable to accommodate each of the plurality of functional rises.

12. The reusable diaper of claim 10, wherein each of the first and second liquid-absorbent flaps includes a first liner and a second liner coupled together to form a pocket structured to facilitate drying of the first and second liners.

13. The reusable diaper of claim 12, wherein for each of the first and second liquid-absorbent flaps, the first and second liners are stitched together along three edges, but not a fourth edge, the fourth edge of the first liner being stitched to the diaper, to thereby form the pocket having an opening defined along the fourth edge of the first and second liners.

14. The reusable diaper of claim 12, wherein the forward waist portion, the rearward waist portion, and the crotch portion are at least partially defined by:
    at least one inner layer configured to be liquid-absorbent; and
    at least one outer layer configured to be substantially liquid-impervious, and coupled to the inner layer; and
    wherein the fixed end portion of the first liquid-absorbent flap is coupled to at least the inner layer.

15. The reusable diaper of claim 14, wherein the first and second liners are formed from one or more of organic cotton material, microfiber terry, and/or suede cloth.

16. The reusable diaper of claim 10, wherein the forward waist portion, the rearward waist portion, and the crotch portion are at least partially defined by:
    at least one outer layer configured to be substantially liquid-impervious,
    at least one inner layer configured to be liquid-absorbent, and coupled to the outer layer and each of the first and second liquid-absorbent flaps, such that the at least one inner layer is between the outer layer and the first and second liquid-absorbent flaps.

17. A reusable diaper, comprising:
    at least one inner layer configured to be liquid-absorbent;
    at least one outer layer configured to be substantially liquid-impervious, and coupled to the inner layer, the at least one outer layer and the at least one inner layer at least partially defining a forward waist portion, a rearward waist portion and a crotch portion of the reusable diaper, the crotch portion disposed between the forward and rearward waist portions;
    a first liquid-absorbent flap having a fixed end portion coupled to the inner layer and a free end portion opposite the fixed end portion, which is not coupled to the reusable diaper, the first liquid-absorbent flap defining a first pocket configured to facilitate drying of the first liquid-absorbent flap;
    a second liquid-absorbent flap having a fixed end portion coupled to the inner layer and a free end portion opposite the fixed end portion, which is not coupled to the reusable diaper, the second liquid-absorbent flap defining a second pocket configured to facilitate drying of the second liquid-absorbent flap;
    wherein the first and second liquid-absorbent flaps at least partially overlap one another along the crotch portion;
    wherein the second liquid-absorbent flap is structured to extend unfolded along the crotch portion toward the rearward waist portion, but not beyond the fixed end portion of the first liquid-absorbent flap when the second liquid-absorbent flap is unfolded and the reusable diaper defines at least one functional rise; and
    wherein the first and second liquid-absorbent flaps are slidable relative to one another.

18. The reusable diaper of claim 17, wherein each of the first and second liquid-absorbent flaps includes a first liner and a second liner coupled together on multiple edges to form the first and second pockets.

19. The reusable diaper of claim 17, wherein the first liquid-absorbent flap is structured to extend unfolded along the crotch portion toward the forward waist portion, but not beyond the forward waist portion, when the first liquid-absorbent flap is unfolded and the reusable diaper defines the at least one functional rise.

\* \* \* \* \*